US009095574B2

(12) United States Patent
Farber et al.

(10) Patent No.: US 9,095,574 B2
(45) Date of Patent: Aug. 4, 2015

(54) METHODS OF TREATING PSORIASIS USING ALLANTOIN

(71) Applicant: Scioderm, Inc., Durham, NC (US)

(72) Inventors: Elliott Farber, Apple Valley, MN (US); Robert Ryan, Durham, NC (US)

(73) Assignee: Scioderm, Inc., Durham, NC (US)

( * ) Notice: Subject to any disclaimer, the term of this patent is extended or adjusted under 35 U.S.C. 154(b) by 0 days.

(21) Appl. No.: 14/062,295

(22) Filed: Oct. 24, 2013

(65) Prior Publication Data

US 2014/0121255 A1    May 1, 2014

Related U.S. Application Data

(62) Division of application No. 13/019,039, filed on Feb. 1, 2011, now abandoned.

(60) Provisional application No. 61/300,627, filed on Feb. 2, 2010.

(51) Int. Cl.
    *A61K 31/4166* (2006.01)
    *A61K 9/00* (2006.01)
    *A61K 9/06* (2006.01)

(52) U.S. Cl.
    CPC .......... *A61K 31/4166* (2013.01); *A61K 9/0014* (2013.01); *A61K 9/06* (2013.01)

(58) Field of Classification Search
    CPC .................................... A61K 31/4166
    USPC ........................................ 514/390
    See application file for complete search history.

(56) References Cited

U.S. PATENT DOCUMENTS

| 3,043,745 A | 7/1962 | Singer et al. |
| 3,830,824 A | 8/1974 | Margraf |
| 3,830,825 A | 8/1974 | Margraf |
| 3,830,908 A | 8/1974 | Klippel et al. |
| 3,856,805 A | 12/1974 | Margraf |
| 3,930,000 A | 12/1975 | Margraf |
| 3,932,627 A | 1/1976 | Margraf |
| 3,954,989 A | 5/1976 | Mecca |
| 4,170,229 A | 10/1979 | Olson |
| 4,184,978 A | 1/1980 | France et al. |
| 4,265,902 A | 5/1981 | Van Ewijk |
| 4,278,664 A | 7/1981 | Van Cleave |
| 4,374,766 A | 2/1983 | Puchalski et al. |
| 4,380,549 A | 4/1983 | Van Scott et al. |
| 4,478,853 A | 10/1984 | Chaussee |
| 4,507,279 A | 3/1985 | Okuyama et al. |
| 4,595,586 A | 6/1986 | Flom |
| 4,670,263 A | 6/1987 | Noorlander |
| 4,707,354 A | 11/1987 | Garlen et al. |
| 4,708,813 A | 11/1987 | Snyder |
| 4,767,618 A | 8/1988 | Grollier et al. |
| 4,806,262 A | 2/1989 | Snyder |
| 4,820,989 A | 4/1989 | Vail, III |
| 4,822,601 A | 4/1989 | Goode et al. |
| 4,826,677 A * | 5/1989 | Mueller et al. ............. 424/78.05 |
| 4,880,621 A | 11/1989 | Grollier et al. |
| 4,933,177 A | 6/1990 | Grollier et al. |
| 4,952,560 A | 8/1990 | Kigasawa et al. |
| 4,981,845 A | 1/1991 | Pereira |
| 5,075,626 A | 12/1991 | Vail, III |
| 5,112,886 A | 5/1992 | Phalangas |
| 5,116,829 A | 5/1992 | Hori et al. |
| 5,122,533 A | 6/1992 | Bar-On et al. |
| 5,176,916 A | 1/1993 | Yamanaka et al. |
| 5,221,533 A | 6/1993 | Perlman |
| 5,296,166 A | 3/1994 | Leong |
| 5,326,557 A | 7/1994 | Glover et al. |
| 5,435,996 A | 7/1995 | Glover et al. |

(Continued)

FOREIGN PATENT DOCUMENTS

| EP | 0 030 157 A1 | 6/1981 |
| EP | 0 242 553 A1 | 10/1987 |

(Continued)

OTHER PUBLICATIONS

Brust, M.D. and Lin, A.N., "Epidermolysis bullosa: practical management and clinical update" *Dermatol. Nursing* 8(2):81-89, Dermatology Nurses' Association, United States (1996).

Cahen, R. and Pessonnier, A., "Etude pharmacologique de l'allantoïnate de dihydroxyaluminium et de l'allantoïnate de chlorhydroxyaluminium. I.—*Toxicité*," *Annales Pharm. Franç.* 20:623-636, Masson et Cie, France (1962).

Cahen, R. and Clement, J.-F., "Etude pharmacologique de l' allantoïnate de dihydroxyaluminium et de l'allantoïnate de chlorhydroxyaluminium. II.—*Etude de l'activité gastrique*," *Annales Pharm. Franç.* 20:693-703, Masson et Cie, France (1962).

Cahen, R. and Pessonnier, A., "Etude pharmacologique de l'allantoïnate de dihydroxyaluminium et de l'allantoïnate de chlorhydroxyaluminium. III.—*Effet anti-ulcéreux*," *Annales Pharm. Franç.* 20:704-713, Masson et Cie, France (1962).

(Continued)

*Primary Examiner* — Jennifer M Kim

(74) *Attorney, Agent, or Firm* — Sterne, Kessler, Goldstein & Fox P.L.L.C.

(57) ABSTRACT

Embodiments herein provide formulations and methods for treatment of inflammatory skin diseases using allantoin in an amount from about 0.5% to about 15.0% by weight. Inflammatory skin diseases treated by embodiments herein include, without limitation, cutaneous porphyria, sclerodema, epidermolysis bulosa, psoriasis, decubitus ulcers, pressure ulcers, diabetic ulcers, venous stasis ulcers, sickle cell ulcers, ulcers caused by burns, eczema, urticaria, atopic dermatitis, dermatitis herpetiform, contact dermatitis, arthritis, gout, lupus erythematosus, acne, alopecia, carcinomas, psoriasis, rosacea, miliaria, skin infections, post-operative care of incisions, post-operative skin care following any variety of plastic surgery operations, skin care following radiation treatment, care of dry, cracked or aged skin and skin lines as well as other conditions affecting the skin and having an inflammatory component, symptoms thereof, or a combination thereof. Symptoms treated may include pain, inflammation, redness, itching, scarring, skin thickening, milia, or a combination thereof.

16 Claims, 15 Drawing Sheets

(56) References Cited

U.S. PATENT DOCUMENTS

| | | |
|---|---|---|
| 5,455,033 A | 10/1995 | Silverman et al. |
| 5,466,718 A | 11/1995 | Nakatsu et al. |
| 5,476,664 A | 12/1995 | Robinson et al. |
| 5,510,712 A | 4/1996 | Sezginer et al. |
| 5,512,200 A | 4/1996 | Garcia |
| 5,536,502 A | 7/1996 | Mulder |
| 5,543,715 A | 8/1996 | Singer et al. |
| 5,563,514 A | 10/1996 | Moulin |
| 5,567,427 A | 10/1996 | Papadakis |
| 5,573,754 A | 11/1996 | Kulkarni et al. |
| 5,578,312 A | 11/1996 | Parrinello |
| 5,608,323 A | 3/1997 | Koelman |
| 5,616,347 A | 4/1997 | Alliger et al. |
| 5,658,559 A | 8/1997 | Smith |
| 5,661,170 A | 8/1997 | Chodosh |
| 5,709,847 A | 1/1998 | Bissett et al. |
| 5,736,128 A | 4/1998 | Chaudhuri et al. |
| 5,753,245 A | 5/1998 | Fowler et al. |
| 5,824,666 A | 10/1998 | Deckner et al. |
| 5,827,870 A | 10/1998 | Chodosh |
| 5,830,483 A | 11/1998 | Seidel et al. |
| 5,849,310 A | 12/1998 | Trinh et al. |
| 5,863,548 A | 1/1999 | Elder |
| 5,871,754 A | 2/1999 | Briggs et al. |
| 5,871,762 A | 2/1999 | Venkitaraman et al. |
| 5,876,736 A | 3/1999 | Cohen et al. |
| 5,885,581 A | 3/1999 | Massand |
| 5,914,116 A | 6/1999 | Suares et al. |
| 5,932,228 A | 8/1999 | Hall et al. |
| 5,952,373 A | 9/1999 | Lanzendörfer et al. |
| 5,958,436 A | 9/1999 | Hahn et al. |
| 5,968,528 A | 10/1999 | Deckner et al. |
| 6,001,377 A | 12/1999 | SaNogueira, Jr. et al. |
| 6,025,721 A | 2/2000 | Vail, III |
| 6,060,061 A | 5/2000 | Breton et al. |
| 6,077,520 A | 6/2000 | Tominaga |
| 6,080,393 A | 6/2000 | Liu et al. |
| 6,086,903 A | 7/2000 | Trinh et al. |
| 6,120,782 A | 9/2000 | Mansouri |
| 6,169,114 B1 | 1/2001 | Yamaguchi et al. |
| 6,174,533 B1 | 1/2001 | SaNogueira, Jr. et al. |
| 6,246,240 B1 | 6/2001 | Vail, III |
| 6,281,236 B1 | 8/2001 | Farber |
| 6,306,915 B1 | 10/2001 | Murata |
| 6,329,413 B1 | 12/2001 | Farber |
| 6,337,065 B1 | 1/2002 | Jacobson et al. |
| 6,351,129 B1 | 2/2002 | Gounot |
| 6,355,259 B1 | 3/2002 | Hiraki et al. |
| 6,531,500 B2 | 3/2003 | Farber |
| 6,545,477 B1 | 4/2003 | Beguin et al. |
| 6,645,507 B2 | 11/2003 | Bettle et al. |
| 6,673,826 B2 | 1/2004 | Farber |
| 6,765,387 B2 | 7/2004 | Prammer |
| 6,864,274 B2 | 3/2005 | Farber |
| 6,896,897 B2 | 5/2005 | Farber |
| 2001/0002290 A1 | 5/2001 | Farber |
| 2001/0003753 A1 | 6/2001 | Farber |
| 2002/0054895 A1 | 5/2002 | Farber |
| 2002/0055531 A1 | 5/2002 | Farber |
| 2002/0102288 A1 | 8/2002 | Farber |
| 2003/0012784 A1 | 1/2003 | Farber |
| 2003/0044435 A1 | 3/2003 | Bettle et al. |
| 2003/0122547 A1 | 7/2003 | Prammer |
| 2003/0129747 A1 | 7/2003 | Frisen |
| 2003/0147968 A1 | 8/2003 | Farber |
| 2003/0157137 A1 | 8/2003 | Farber |
| 2003/0162821 A1 | 8/2003 | Farber |
| 2004/0082634 A1 | 4/2004 | Farber |
| 2004/0180853 A1 | 9/2004 | Farber |
| 2006/0093636 A1 | 5/2006 | Farber |
| 2006/0134149 A1 | 6/2006 | Farber |
| 2008/0075747 A1 | 3/2008 | Farber |
| 2008/0269308 A1* | 10/2008 | Farber ............ 514/390 |
| 2009/0170919 A1 | 7/2009 | Farber |
| 2011/0152335 A1 | 6/2011 | Farber |
| 2011/0165260 A1 | 7/2011 | Farber |
| 2012/0065238 A1 | 3/2012 | Farber |
| 2012/0165379 A1 | 6/2012 | Farber |
| 2013/0030030 A1 | 1/2013 | Farber |
| 2013/0345274 A1 | 12/2013 | Farber |
| 2014/0005242 A1 | 1/2014 | Farber |
| 2014/0010771 A1 | 1/2014 | Farber |
| 2014/0135372 A1 | 5/2014 | Farber |
| 2014/0142151 A1 | 5/2014 | Farber |
| 2014/0194482 A1 | 7/2014 | Farber et al. |

FOREIGN PATENT DOCUMENTS

| | | |
|---|---|---|
| EP | 0 380 157 A1 | 8/1990 |
| EP | 0 487 404 A1 | 11/1991 |
| EP | 1 004 289 A2 | 11/1999 |
| EP | 2 172 106 A1 | 4/2010 |
| FR | 2 405 068 A1 | 5/1979 |
| GB | 1 202 635 | 8/1970 |
| GB | 1 346 544 | 2/1974 |
| JP | 58-140013 A | 8/1983 |
| JP | 63-159317 A | 7/1988 |
| JP | 64-58165 A | 3/1989 |
| JP | 4-208219 A | 7/1992 |
| WO | WO 90/09779 A1 | 9/1990 |
| WO | WO 98/02138 A1 | 1/1998 |
| WO | WO 98/29085 A2 | 7/1998 |
| WO | WO 00/79307 A1 | 12/2000 |
| WO | WO 01/06991 A1 | 2/2001 |
| WO | WO 01/87232 A2 | 11/2001 |
| WO | WO 01/87301 A1 | 11/2001 |
| WO | WO 03/017941 A2 | 3/2003 |
| WO | WO 03/041651 A2 | 5/2003 |
| WO | WO 03/041688 A1 | 5/2003 |
| WO | WO 03/054585 A1 | 7/2003 |

OTHER PUBLICATIONS

Cahen, R. and Pessonnter, A., "Etude pharmacologique de l'allantoïnate de dihydroxyaluminium et de l'allantoïnate de chlorhydroxyaluminium. IV.—*Effet sur l'ulcère médicamenteux expérimental,*" *Annales Pharm. Franç.* 21:215-222, Masson et Cie, France (1963).

Čajkovac, M., et al., "Influence of emulsoid vehicle on the release and activity of allantoin," *Pharmazie* 47:39-43, Govi-Verlag Pharmazautischer Verlag, Germany (1992) (Abstract).

"Chapter 34: Instrumental Methods of Analysis," in *Remington: The Science and Practice of Pharmacy*, 19th Ed., Gennaro, A.R., ed., pp. 639-640,1380, John Wiley & Sons Australia, Limited, Australia (1995).

Debray, Ch., et al., "Étude de Dérivés Allantoïniques de l'Aluminium dans la Thérapeutique des Affections Gastro-duodénales," *Presse Méd.* 70:2643-2644, Masson et Cie, France (1962).

Greenbaum, F.R., "The Story of Allantoin," *Am. J. Pharm.* 112:205-216, Philadelphia College of Pharmacy and Science, United States (1940).

Hoffman, D., *The Complete Illustrated Holistic Herbal: A Safe and Practical Guide to Making and Using Herbal Remedies*, Elemental Books, pp. 63, 104, United States (1996).

Lesser, M.A., "Allantoin," *Drug and Cosmetic Industry* 42:451-456, 469, The Drug and Cosmetic Industry, United States (1938).

Levan, P., et al., "The Use of Silicones in Dermatology," *California Medicine* 81(3):210-213, California Medical Association, United States (1954).

Lubowe, I.I. and Mecca, S.B., "Allantoin and Aluminum Derivatives in Dermatological Applications," *Drug and Cosmetic Industry* 84: 36, 37, 117, The Drug and Cosmetic Industry, United States (1959).

Maragakis, M., et al., "Possibilities of Scar Treatment After Thoracic Surgery," *Drugs Exp. Clin.Res.* 21:199-206, (1995), Abstract, 1 Page, accessed at http://www.paperchase.com/scripts/mgwms32.dll/ on Oct. 4, 2011.

Margraf, H.W. and Covey, Jr., T.H., "A Trial of Silver—Zinc-Allantoinate in the Treatment of Leg Ulcers," *Arch Surg* 112:699-704, American Medical Association, United States (1977).

Mecca, S.B., "Allantoin and the Newer Aluminum Allantoinates," *Proc. Scient. Sect. Toilet Goods Assoc.* 31:1-6, The Toilet Goods Association, United States (1959).

(56) References Cited

OTHER PUBLICATIONS

Mecca, S.B., "The Function and Applicability of the Allantoins," *Proc. Scient. Sect. Toilet Goods Assoc.* 39:7-15, The Toilet Goods Association, United States (1963).
The Merck Index: *An Encyclopedia of Drugs, Chemicals and Biologicals*, Twelfth Edition, Smith, A., et al., Eds., pp. 128, 735, 1213, Merck & Company, Inc., United States (1996).
National Institute of Standards and Technology, Material Measurement Laboratory, Standard Reference Data Program, CAS RN 99-76-3 and CAS RN 94-13-3, U.S. Secretary of Commerce on behalf of the United States of America (2011).
Alphosyl Cream and Alphosyl Lotion Product Information, South African Electronic Package Inserts, Stafford-Miller Ltd, England (1975).
Arola Rose Balm Product Information, South African Electronic Package Inserts, Pharmaceutical Enterprises (Pty) Ltd, South Africa (1993).
Arola Rosebaum Product Information, Supramed Limited, (1986).
Clearasil Medicated Facial Cleanser Product Information, South African Electronic Package Inserts, Procter & Gamble SA (Pty) Ltd., South Africa (1994).
Stinco, G., et al., "Dermatite seborroica del volto trattata con una crema a base di furalglucitolo," *Derm. Clin.* 18:78-81, Centro Italiano Congressi, Italy (1998).
Westman, M., "Galactoarabinan: An Exfoliant for Human Skin," *Cosmetics and Toiletries* 114(8):63-72, Allured Publishing Corp., United States (1999) (Abstract).
Willital, G.H. and Heine, H., "Efficiency of Contractubex® Gel in the Treatment of Fresh Scars After Thoracic Surgery in Children and Adolescents," *Int. J. Clin. Pharmacol. Res.* 14(5/6):193-202, Bioscience Ediprint Inc., Switzerland (1994).
International Search Report dated Oct. 12, 2000 for PCT/US00/19859.
International Search Report dated Aug. 24, 2001 for PCT/US01/14899.
International Search Report dated Oct. 24, 2001 for PCT/US01/15102.
International Search Report dated Jan. 31, 2003 for PCT/US02/36438.
International Search Report dated Jun. 3, 2003 for PCT/US02/26928.
International Search Report dated Jul. 14, 2003 for PCT/US02/36439.
Supplementary European Search Report dated Nov. 26, 2004 for EP 00 95 0494.
European Search Report dated Feb. 24, 2010 for EP 07 02 1279.
Almeyda, J., et al., "Treatment of Psoriasis: Comparative Study Using Allantoin Coal Tar Extract Combined with Hydrocortisone and Betamethasone Valerate," *Brit. J. Clin. Pract.* 33(4):106-108, Harvey & Blythe Ltd., England (1979).
Berthemy, A., et al., "Quantitative determination of an extremely polar compound allantoin in human urine by LC-MS/MS based on the separation on a polymeric amino column," *J. Pharm. Biomed. Anal.* 19:429-434, Elsevier Science B.V., England (1999).
Brookes, D.B., et al., "Comparison of Tretinoin and a Composite Formulation in the Treatment of Acne," *Brit. J. Clin. Pract.* 32(12):349-352, Harvey & Blythe Ltd., England (1978).
Castro, A H. F., et al., "Influence of Photoperiod on the Accumulation of Allantoin in Comfrey Plants," *R. Bras. Fisiol. Veg.* 13(1):49-54, Sociedade Brasileira de Fisiologia Vegetal, Brazil (2001).
Fisher, A. A., "Allantoin: A Non-Sensitizing Topical Medicament Therapeutic Effects of the Addition of 5 Percent Allantoin to Vaseline," *Cutis* 27:230-234, Cahners Pub. Co., United States (1981).
Fraser, N. B., et al., "Treatment of acne vulgaris comparing two similar lotion formulations, one with ('Actinac') and one without chloramphenicol," *Curr. Med. Res. Opin.* 6(7):461-465, M. D. Promotions, ltd., United Kingdom (1980).
Garnik, J. J., et al., "Effectiveness of a medicament containing silicon dioxide, aloe, and allantoin on aphthous stomatitis," *Oral. Surg. Oral. Med. Oral. Pathol. Oral. Radiol. Endod.* 86(5):550-556, Elsevier, United States (1998).

Harrington, C. I., "Low concentration dithranol and coal tar (Psorin) in psoriasis: a comparison with alcoholic coal tar extract and allantoin (Alphosyl)," *Brit. J. Clin. Pract.* 43(1):27-29, Harvey & Blythe Ltd., England (1989).
Henning, T., "Evaluation of the Efficacy of Allantoin," *Euro. Cosmet.* 2:20-22 (2001).
Kaplan, T., "The Allantoin Treatment of Ulcers," *JAMA* 108(12):968-969, American Medical Association, United States (1937).
Klippel, A. P., et al., "The Use of Silver-Sinc-Allantoin Powder for the Prehospital Treatment of Burns," *JACEP* 6(5):184-186, American College of Emergency Physicians, United States (1966).
Lunan, H.N., "Topical treatment of the burn patient," *Am. J. Hosp. Pharm.* 32:599-605, American Society of Hospital Pharmacists, Inc., United States (1975).
Meixell, D. W., et al., "The Allantoins," *J. Am. Podiatry Assoc.* 56(8):357-364, American Podiatry Association, United States (1966).
Parish, L. C., et al., "Oxipor VHC Lotion Versus Tegrin in the Treatment of Psoriasis," *Cutis* 30(5):676-678, Quadrant HealthCom Inc., United States (1982).
Pavillard, E. R., et al., "An Antibiotic from Maggots," *Nature* 180:916-917, Nature Publishing Group, England (1957) (abstract).
Pavitt, D. V., et al., "Assay of serum allantoin in humans by gas chromatography-mass spectrometry," *Clinica. Chimica. Acta.* 318:63-70, Elsevier, Netherlands (2002).
Robinson, W., "Stimulation of Healing in Non-Healing Wounds: By Allantoin Occurring in Maggot Secretions and of Wide Biological Distribution," *J. Bone Joint Surg. Am.* 17:267-271, The Journal of Bone and Joint Surgery, United States (1935).
Sheker, K. M., et al., "Silver Allantoinate for the Topical Treatment of Burns," *Am. J. Hosp. Pharm.* 29:852-855, American Society of Hospital Pharmacists, United States (1972).
Thompson, J. E., et al., "Topical Use of Aloe Vera Derived Allantoin Gel in Otolaryngology," *Ear Nose Throat J.*. 70(1):56, Medquests Communications, United States (1991).
Van Der Cammen, T. J. M., et al., "Prevention of pressure sores. A comparison of new and old pressure sore treatments," *Brit. J. Clin. Pract.* 41(11):1009-1011, Harvey & Blythe Ltd., England (1987).
Wadhams, P. S., et al., "Efficacy of a Surfactant, Allantoin, and Benzalkonium Chloride Solution for Onychomycosis: Preliminary Results of Treatment with Periodic Debridement," *J. Am. Podiatr. Med. Assoc.* 89(3):124-130, American Podiatry Association, United States (1999).
Young, E. G., et al., "The Estimation of Allantoin in Blood," *J. Biol. Chem.* 152:245-253, American Society for Biochemistry and Molecular Biology, United States (1944).
Young, E., "Allantoin in Treatment of Psoriasis," *Dermatologica* 147(5):338-341, Karger, Switzerland (1973).
"Committee for Veterinary Medical Products—Allantoin—Summary Report," EMEA/MRL/804/01-Final, Oct. 2001, The European Agency for Evaluation of Medicinal Products Veterinary Medicines and Inspections (EMEA), United Kingdom (2001).
Supplementary European Search Report for EP 01 93 5174, European Patent Office, Germany, dated Dec. 17, 2004.
Office Action mailed Apr. 8, 2013, in U.S. Appl. No. 13/019,039, inventor Elliot Farber, filed Feb. 1, 2011.
Office Action mailed Jan. 24, 2014, in U.S. Appl. No. 13/019,039, inventor Elliot Farber, filed Feb. 1, 2011.
Office Action mailed Dec. 3, 2013, in U.S. Appl. No. 14/018,050, inventor Elliot Farber, filed Sep. 4, 2013.
Office Action mailed Dec. 3, 2013, in U.S. Appl. No. 14/018,167 inventor Elliot Farber, filed Sep. 4, 2013.
Office Action mailed Apr. 10, 2014, in U.S. Appl. No. 14/147,425 inventor Elliot Farber, filed Jan. 3, 2014.
Office Action mailed Jul. 9, 2014, in U.S. Appl. No. 14/223,183 inventor Elliot Farber, filed Mar. 24, 2014 (Not Published).
Co-pending Unpublished Application, U.S. Appl. No. 14/223,183, inventor Elliott Farber, filed Mar. 24, 2014 (Not Published).
Co-pending Unpublished Application, U.S. Appl. No. 14/226,419, inventor Elliott Farber, filed Mar. 26, 2014 (Not Published).
§358.710: Active ingredients for the control of dandruff, seborrheic dell latitis, or psoriasis, *21 CFR Ch. 1*:324, Food and Drug Administration, United States (Apr. 1, 2013).

(56) References Cited

OTHER PUBLICATIONS

Herdenstam, C.G., "Allantoin in the Treatment of Psoriasis: A Double Blind Study," *Acta Dermato-Venereologica* 39:216-224, Society for the Publication of Acta Dellnalo-Venereologica, Sweden (1959).

Clyman, S.G., "Clinical Experience with a New Preparation for the Treatment of Psoriasis: A Paired Comparative Study," *Ann N Y Acad Sci* 73(5):1032-1037, New York Academy of Sciences, United States (1958).

Bleiberg, J., "Clinical Experience with a New Preparation for the Treatment of Psoriasis," *Ann N Y Acad Sci* 73(5):1028-1031, New York Academy of Sciences, United States (1958).

Department of Health and Human Services, "Dandruff, Seborrheic Dermatitis, and Psoriasis Drug Projects for Over-the-Counter Human Use; Final Monograph," *Federal Register* 56(233).63554-63569, Food and Drug Administration, United States (1991).

\* cited by examiner

| ingredient | 1-206A | 1-192A | 1-196A | 1-204A | 1-133C | 1-139E | 1-81B | 1-135C | 1-135G | 1-81G | 1-153H |
|---|---|---|---|---|---|---|---|---|---|---|---|
| allantoin | 0.00% | 3.00% | 6.00% | 9.00% | 0.00% | 0.90% | 1.50% | 3.00% | 6.00% | 9.00% | 9.00% |
| water | 69.16% | 67.41% | 65.11% | 63.71% | 69.71% | 69.21% | 68.68% | 67.01% | 63.98% | 58.98% | 61.78% |
| cetyl alcohol | 5.00% | 4.20% | 3.60% | 2.50% | 4.45% | 4.35% | 4.20% | 3.50% | 3.23% | 4.20% | 2.70% |
| stearyl alcohol | 2.45% | 2.00% | 1.70% | 1.20% | 2.25% | 2.35% | 2.00% | 1.70% | 1.50% | 2.00% | 1.20% |
| beeswax | 1.90% | 1.90% | 2.00% | 2.00% | 1.90% | 1.90% | 1.90% | 2.50% | 2.75% | 3.00% | 2.75% |
| sodium lauryl sulfate—30% solution | 1.90% | 1.90% | 2.00% | 2.00% | 1.90% | 1.90% | 1.90% | 2.50% | 2.75% | 3.00% | 2.75% |
| citric acid | 0.09% | 0.09% | 0.09% | 0.09% | 0.09% | 0.09% | 0.12% | 0.09% | 0.09% | 0.12% | 0.12% |
| lanolin oil | 10.60% | 10.60% | 10.60% | 10.60% | 10.60% | 10.60% | 10.60% | 10.60% | 10.60% | 10.60% | 10.60% |
| propylene glycol | 5.70% | 5.70% | 5.70% | 5.70% | 5.70% | 5.70% | 5.70% | 5.70% | 5.70% | 5.70% | 5.70% |
| tetrasodium EDTA | 0.15% | 0.15% | 0.15% | 0.15% | 0.15% | 0.15% | 0.15% | 0.15% | 0.15% | 0.15% | 0.15% |
| cod liver oil | 2.00% | 2.00% | 2.00% | 2.00% | 2.00% | 2.00% | 2.00% | 2.00% | 2.00% | 2.00% | 2.00% |
| BHT | 0.50% | 0.50% | 0.50% | 0.50% | 0.50% | 0.50% | 0.50% | 0.50% | 0.50% | 0.50% | 0.50% |
| methylparaben | 0.30% | 0.30% | 0.30% | 0.30% | 0.30% | 0.30% | 0.30% | 0.30% | 0.30% | 0.30% | 0.30% |
| propylparaben | 0.25% | 0.25% | 0.25% | 0.25% | 0.25% | 0.25% | 0.25% | 0.25% | 0.25% | 0.25% | 0.25% |
| fragrance | 0.00% | 0.00% | 0.00% | 0.00% | 0.20% | 0.20% | 0.20% | 0.20% | 0.20% | 0.20% | 0.20% |
| total | 100.0% | 100.0% | 100.0% | 100.0% | 100.0% | 100.0% | 100.0% | 100.0% | 100.0% | 100.0% | 100.0% |

FIGURE 1

Total Absorption Results Across Sub-Studies

Percutaneous Absorption through Various Barriers over 48 hours from a Single Application. Mean ± SE as Total Mass (μg)

| Study | 0.5% (A.S. 1-139E) | 1.5% (A.S. 1-81B) | 3% (A.S. 1-135C) | 6% (A.S. 1-135G) | 9% (A.S. 1-81G) |
|---|---|---|---|---|---|
| Membrane* | 196.48 ± 45.30 | 792.25 ± 39.83 | 1399.49 ± 205.99 | 1348.30 ± 201.39 | 2294.42 ± 552.35 |
| Abraded Porcine | 38.80 ± 18.34 | 68.91 ± 31.01 | 95.74 ± 25.55 | 109.52 ± 39.91 | 103.70 ± 34.23 |
| Un-abraded Porcine | nd | nd | 38.64 ± 15.24 | nd | nd |
| Full thickness Human skin | 12.05 ± 1.88 | 19.23 ± 5.61 | 32.04 ± 11.42 | 41.57 ± 8.43 | 22.74 ± 12.15 |
| Dermis only Human skin | 412.60 ± 95.30 | 910.51 ± 73.99 | 1434.19 ± 95.71 | 1990.40 ± 167.34 | 2718.74 ± 548.33 |

* Membrane study was conducted over 24 hours.
nd = not done.

Total Absorption Results 9% Allantoin Supplement Study

Percutaneous Absorption through Dermatomed human cadaver skin over 48 hours from a Single Application. Mean ± SE as Total Mass (μg)

| Study | 9% (A.S. 1-91G) | 9% (A.S. 1-153H) |
|---|---|---|
| Dermatomed human skin | 40.21 ± 9.65 | 92.48 ± 22.0 |

FIGURE 3

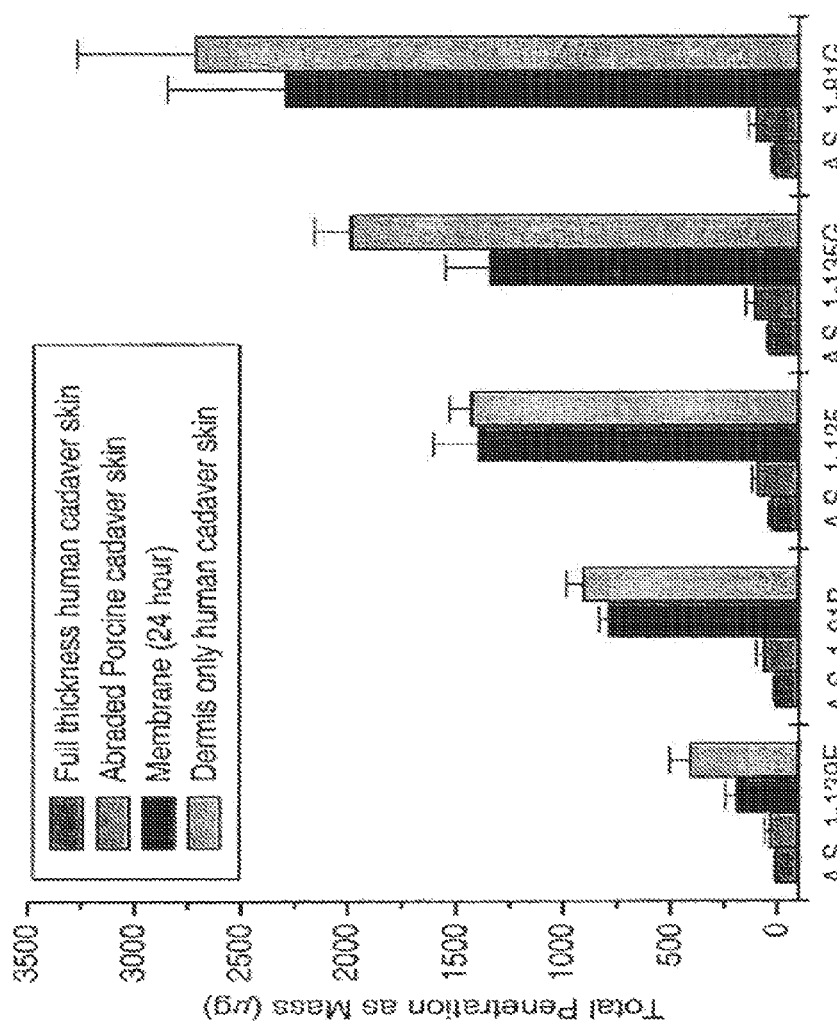

Mean Flux (μg/cm²/hr) Results: Membrane Summary

Release of Allantoin through a porous membrane over 48 hours. (Mean ± SD)

| Time (hr)* | 0.5% (A.S. 1-139E) | 1.5% (A.S. 1-81B) | 3% (A.S. 1-135C) | 6% (A.S. 1-135G) | 9% (A.S. 1-81G) |
|---|---|---|---|---|---|
| 0.25 | 112.12 ± 75.87 | 377.84 ± 35.10 | 633.93 ± 127.32 | 287.46 ± 362.27 | 610.21 ± 605.20 |
| 0.75 | 93.00 ± 49.93 | 215.88 ± 22.67 | 402.16 ± 55.21 | 408.49 ± 166.03 | 630.56 ± 154.25 |
| 1.5 | 42.93 ± 10.65 | 165.81 ± 29.24 | 248.68 ± 41.41 | 258.52 ± 73.87 | 353.78 ± 84.02 |
| 3 | 21.40 ± 4.53 | 97.90 ± 13.78 | 142.69 ± 19.55 | 162.74 ± 27.27 | 250.89 ± 60.86 |
| 6 | 7.49 ± 3.22 | 46.98 ± 2.90 | 74.35 ± 15.78 | 87.38 ± 25.88 | 139.12 ± 91.01 |
| 9.5 | 4.67 ± 1.91 | 25.68 ± 4.03 | 55.74 ± 10.68 | 49.37 ± 26.77 | 46.41 ± 47.57 |
| 17.5 | 1.02 ± 0.35 | 5.14 ± 2.42 | 17.89 ± 4.54 | 15.50 ± 13.03 | 28.92 ± 16.04 |

*Time as midpoint between samples.

Allantoin Total Absorption Results

Absorption of Allantoin through a Porous Membrane over 24 hours from a Single Application. Mean ± SD as Percent of Applied Dose and Total Mass (μg)

| Parameter | 0.5% (A.S. 1-139E) | 1.5% (A.S. 1-81B) | 3% (A.S. 1-135C) | 6% (A.S. 1-135G) | 9% (A.S. 1-81G) |
|---|---|---|---|---|---|
| Total Absorption (%) | 49.12 ± 11.32 | 66.02 ± 3.32 | 58.31 ± 8.58 | 28.09 ± 4.20 | 31.87 ± 7.67 |
| Total Absorption (μg) | 196.48 ± 45.30 | 792.25 ± 39.83 | 1399.49 ± 205.99 | 1348.30 ± 201.39 | 2294.42 ± 552.35 |
| Replicates | 3 | 3 | 4 | 6 | 5 |

FIGURE 7

Mean Flux (μg/cm²/hr) Results: Porcine Cadaver Skin

Percutaneous Absorption of Allantoin through Abraded and Un-Abraded Porcine Cadaver Skin.
(Mean ± SE)

| Time (hr)* | 0.5% (A.S. 1-139E) | 1.5% (A.S. 1-81B) | 3% (A.S. 1-135C) | 8% (A.S. 1-135C) | 8% (A.S. 1-81G) | 3% (A.S. 1-135C) Un-Abraded |
|---|---|---|---|---|---|---|
| 0.5 | 0.022 ± 0.011 | 0.078 ± 0.048 | 0.016 ± 0.010 | 0.010 ± 0.006 | 0.024 ± 0.014 | 0.002 ± 0.001 |
| 2 | 0.019 ± 0.008 | 0.360 ± 0.290 | 0.045 ± 0.019 | 0.073 ± 0.025 | 0.060 ± 0.008 | 0.004 ± 0.003 |
| 4 | 0.045 ± 0.015 | 0.485 ± 0.325 | 0.164 ± 0.091 | 0.256 ± 0.086 | 0.239 ± 0.013 | 0.016 ± 0.011 |
| 6 | 0.111 ± 0.034 | 0.761 ± 0.452 | 0.419 ± 0.211 | 0.548 ± 0.155 | 0.519 ± 0.021 | 0.032 ± 0.019 |
| 8.5 | 0.537 ± 0.094 | 1.978 ± 1.046 | 1.454 ± 0.424 | 2.158 ± 0.166 | 2.009 ± 0.204 | 0.211 ± 0.083 |
| 17 | 1.075 ± 0.353 | 2.341 ± 1.022 | 2.831 ± 0.862 | 3.802 ± 0.952 | 3.082 ± 0.876 | 0.642 ± 0.260 |
| 27 | 1.135 ± 0.638 | 1.769 ± 1.285 | 2.366 ± 1.269 | 3.402 ± 2.266 | 2.756 ± 2.125 | 1.085 ± 0.686 |
| 39 | 1.370 ± 0.721 | 1.861 ± 0.670 | 3.268 ± 0.706 | 3.057 ± 1.237 | 3.448 ± 1.051 | 1.781 ± 0.649 |

*Time as midpoint between samples.

Allantoin Total Absorption Results

Percutaneous Absorption of Allantoin through Abraded and Un-Abraded Porcine Cadaver Skin
over 48 hours from a Single Application. Mean ± SE as Percent of Applied Dose and Total Mass (μg).

| Parameter | 0.5% (A.S. 1-139E) | 1.5% (A.S. 1-81B) | 3% (A.S. 1-135C) | 6% (A.S. 1-135C) | 9% (A.S. 1-81G) | 3% (A.S. 1-135C) Un-Abraded |
|---|---|---|---|---|---|---|
| Total Absorption (%) | 9.70 ± 4.58 | 5.74 ± 2.58 | 3.99 ± 1.07 | 2.28 ± 0.82 | 1.44 ± 0.48 | 1.61 ± 0.64 |
| Total Absorption (μg) | 38.80 ± 18.34 | 68.91 ± 31.01 | 95.74 ± 25.55 | 109.52 ± 39.31 | 103.70 ± 34.23 | 38.64 ± 15.24 |

FIGURE 9

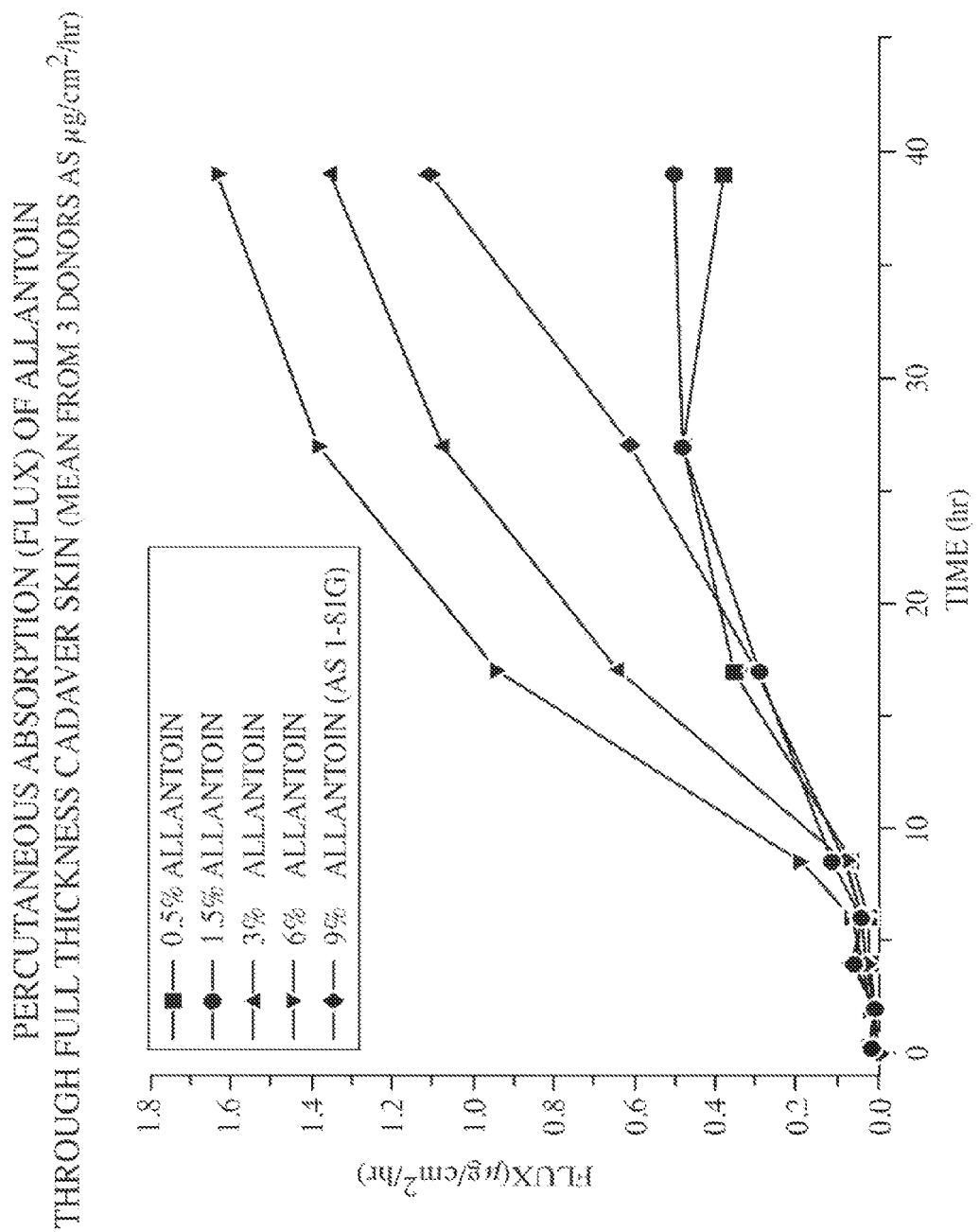

Mean Flux (μg/cm²/hr) Results: Full Thickness Human Cadaver Skin

Percutaneous Absorption of Allantoin through Full Thickness Human Cadaver Skin
(Mean ± SE)

| Time (hr)* | 0.5% (A.S. 1-139E) | 1.5% (A.S. 1-81B) | 3% (A.S. 1-135C) | 6% (A.S. 1-135G) | 9% (A.S. 1-81G) |
|---|---|---|---|---|---|
| 0.5 | 0.000 ± 0.000 | 0.000 ± 0.000 | 0.000 ± 0.000 | 0.005 ± 0.003 | 0.020 ± 0.020 |
| 2 | 0.001 ± 0.001 | 0.012 ± 0.006 | 0.000 ± 0.000 | 0.019 ± 0.019 | 0.019 ± 0.019 |
| 4 | 0.035 ± 0.021 | 0.046 ± 0.037 | 0.004 ± 0.004 | 0.039 ± 0.036 | 0.024 ± 0.022 |
| 6 | 0.021 ± 0.014 | 0.040 ± 0.026 | 0.003 ± 0.003 | 0.068 ± 0.043 | 0.031 ± 0.020 |
| 8.5 | 0.062 ± 0.048 | 0.114 ± 0.049 | 0.081 ± 0.038 | 0.183 ± 0.038 | 0.077 ± 0.009 |
| 17 | 0.355 ± 0.086 | 0.286 ± 0.114 | 0.537 ± 0.253 | 0.948 ± 0.282 | 0.305 ± 0.126 |
| 27 | 0.484 ± 0.087 | 0.479 ± 0.205 | 1.074 ± 0.315 | 1.390 ± 0.251 | 0.613 ± 0.208 |
| 39 | 0.383 ± 0.071 | 0.507 ± 0.250 | 1.357 ± 0.529 | 1.640 ± 0.378 | 1.116 ± 0.689 |

*Time as midpoint between samples.

Allantoin Total Absorption Results: Full Thickness Human Cadaver Skin

Percutaneous Absorption of Allantoin through Full Thickness Human Cadaver Skin over 48 hours from a Single Application. Mean ± SE as Percent of Applied Dose and Total Mass (μg)

| Parameter | 0.5% (A.S. 1-139E) | 1.5% (A.S. 1-81B) | 3% (A.S. 1-135C) | 6% (A.S. 1-135G) | 9% (A.S. 1-81G) |
|---|---|---|---|---|---|
| Total Absorption (%) | 2.87 ± 0.61 | 1.07 ± 0.49 | 1.29 ± 0.51 | 0.83 ± 0.21 | 0.31 ± 0.17 |
| Total Absorption (μg) | 12.05 ± 1.88 | 13.23 ± 5.61 | 32.04 ± 11.42 | 41.57 ± 8.43 | 22.74 ± 12.15 |

FIGURE 11

Mean Flux (μg/cm²/hr) Results: Isolated Dermis Layer from Human Cadaver Skin

Percutaneous Absorption of Allantoin through Dermis Layer from Human Cadaver Skin (Mean ± SE)

| Time (hr)* | 0.5% (A.S. 1-139E) | 1.5% (A.S. 1-61B) | 3% (A.S. 1-135C) | 6% (A.S. 1-135G) | 9% (A.S. 1-81G) |
|---|---|---|---|---|---|
| 0.5 | 30.09 ± 15.42 | 96.71 ± 14.37 | 96.78 ± 42.79 | 98.84 ± 35.43 | 179.27 ± 50.63 |
| 2 | 51.31 ± 8.31 | 114.48 ± 13.76 | 202.84 ± 24.49 | 183.99 ± 70.67 | 199.78 ± 73.93 |
| 4 | 55.17 ± 9.26 | 105.08 ± 12.15 | 146.83 ± 9.45 | 168.22 ± 38.51 | 206.07 ± 63.24 |
| 6 | 72.79 ± 41.04 | 83.21 ± 19.25 | 86.21 ± 15.23 | 133.60 ± 17.64 | 162.54 ± 29.53 |
| 8.5 | 13.84 ± 2.66 | 36.14 ± 3.61 | 55.64 ± 2.01 | 94.79 ± 9.35 | 121.10 ± 22.54 |
| 17 | 3.50 ± 1.23 | 13.66 ± 1.51 | 25.88 ± 0.82 | 42.98 ± 2.09 | 59.38 ± 9.90 |
| 27 | 1.74 ± 0.47 | 8.92 ± 1.41 | 16.21 ± 0.60 | 33.03 ± 3.57 | 55.24 ± 8.85 |
| 39 | 1.46 ± 1.21 | 4.60 ± 0.94 | 10.59 ± 0.62 | 16.51 ± 2.86 | 32.01 ± 3.00 |

*Time as midpoint between samples.

Allantoin Total Absorption Results: Isolated Dermis Layer from Human Cadaver Skin Percutaneous Absorption of Allantoin through Dermis Layer from Human Cadaver Skin over 48 hours from a Single Application. Mean ± SE as Percent of Applied Dose and Total Mass (μg)

| Parameter | 0.5% (A.S. 1-139E) | 1.5% (A.S. 1-81B) | 3% (A.S. 1-135C) | 6% (A.S. 1-135G) | 9% (A.S. 1-81G) |
|---|---|---|---|---|---|
| Total Absorption (%) | 93.09 ± 14.17 | 70.02 ± 1.43 | 58.91 ± 7.44 | 39.17 ± 5.78 | 36.22 ± 9.11 |
| Total Absorption (μg) | 412.60 ± 96.30 | 910.51 ± 73.89 | 1434.19 ± 95.71 | 1990.40 ± 167.34 | 2718.74 ± 548.33 |

FIGURE 13

Mean Flux (μg/cm²/hr) Results: 9% Allantoin Through Dermatomed
Human Cadaver Skin (Supplement Study)
Percutaneous Absorption of Allantoin through Dermatomed Human Cadaver Skin
(Mean ± SE)

| Time (hr)* | 9% (A.S. 1-153H) | 9% (A.S. 1-81G) |
|---|---|---|
| 0.5 | 1.301 ± 1.103 | 0.570 ± 0.089 |
| 2 | 0.983 ± 0.742 | 0.435 ± 0.088 |
| 4 | 0.592 ± 0.260 | 0.235 ± 0.024 |
| 6 | 0.937 ± 0.059 | 0.260 ± 0.033 |
| 8.5 | 1.657 ± 0.270 | 0.395 ± 0.039 |
| 17 | 3.060 ± 0.549 | 0.922 ± 0.233 |
| 27 | 2.931 ± 0.828 | 1.316 ± 0.479 |
| 39 | 2.438 ± 0.810 | 1.429 ± 0.347 |

*Time as midpoint between samples.

9% Allantoin Total Absorption Results (Supplement Study)
Percutaneous Absorption of Allantoin through Dermatomed Human Cadaver Skin
over 48 hours from a Single Application. Mean ± SE as Percent of Applied Dose and Total Mass (μg)

| Parameter | 9% (A.S. 1-153H) | 9% (A.S. 1-81G) |
|---|---|---|
| Total Absorption (%) | 20.55 ± 4.88 | 8.94 ± 2.15 |
| Total Absorption (μg) | 92.46 ± 21.97 | 40.21 ± 9.65 |

FIGURE 15

METHODS OF TREATING PSORIASIS USING ALLANTOIN

CROSS-REFERENCE TO RELATED APPLICATIONS

This application is a divisional of U.S. application Ser. No. 13/019,039, filed Feb. 1, 2011, which claims priority from U.S. Provisional Application No. 61/300,627 filed Feb. 2, 2010 entitled "Compositions and Methods for Treatment of Inflammatory Skin Conditions Using Allantoin," each of which is incorporated herein by reference in its entirety.

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISC

Not applicable

BACKGROUND

Not applicable

BRIEF SUMMARY OF THE INVENTION

Embodiments of the present invention relate generally to compositions comprising allantoin that can be used to treat individuals affected with inflammatory skin conditions. The compositions are preferably formulated as topical formulations.

In one aspect, formulations of allantoin comprising from about 2.5% to about 15% of allantoin by weight and a pharmaceutically acceptable excipient are provided. In some embodiments, the amount of allantoin is not 1.5% by weight or less of the composition. In some embodiments, the amount of allantoin is not 2.0% by weight or less of the composition. In embodiments, the formulation further comprises an emollient, an emulsifier, a solvent, a pH modifier, a solubilizing agent, an antioxidant, a preservative, a chelating agent, an additive, a viscosity agent or a combination thereof. In some embodiments, the formulation comprises, allantoin in an amount from about 2.5% to about 15% by weight of the formulation, water, cetyl alcohol, stearyl alcohol, beeswax, sodium lauryl sulfate in an about 30% solution, citric acid, lanolin oil, propylene glycol, cod liver oil, butylated hydroxytoluene, methylparaben, propylparaben or a combination thereof. In an embodiment, the formulation may comprise allantoin in an amount of from about 2.5% to about 15%; water in an amount from about 40% to about 90%; cetyl alcohol in an amount from about 0.5% to about 15%; stearyl alcohol in an amount from about 1% to about 3%; beeswax in an amount from about 1.5% to about 3%; sodium lauryl sulfate in a 30% solution in an amount from about 1.5% to about 3%; citric acid in an amount from about 0.5% to about 0.2%; lanolin oil in an amount from about 5% to about 15%; propylene glycol in an amount from about 2% to about 8%; tetrasodium EDTA in an amount from about 0.05% to about 0.5%; cod liver oil in an amount from about 0.05% to about 5%; butylated hydroxytoluene in an amount from about 0.05% to about 1%; methylparaben in an amount from about 0.05% to about 0.5%; propylparaben in an amount from about 0.05% to about 0.5% by weight of the formulation or a combination thereof. In embodiments, the formulation optionally includes tetrasodium EDTA. In embodiments, the tetrasodium EDTA may be present in an amount from about 0.05% to about 0.5% by weight of the formulation. In embodiments, the formulation optionally includes a fragrance. In some embodiments, allantoin may be present in an amount from about 1.5% to about 15%, from about 2.0% to about 15%, from about 2.5% to about 15% or from about 3.0% to about 15% by weight of the formulation. In some embodiments, the amount of allantoin is not 1.5% by weight or less of the composition. In some embodiments, the amount of allantoin is not 2.0% by weight or less of the composition.

In another aspect, formulations of allantoin comprising about 3.0% of allantoin, water, cetyl alcohol, stearyl alcohol, beeswax, sodium lauryl sulfate in an about 30% solution, citric acid, lanolin oil, propylene glycol, tetrasodium EDTA, cod liver oil, butylated hydroxytoluene, methylparaben, and propylparaben are provided. In another aspect, formulations of allantoin comprising about 6.0% of allantoin, water, cetyl alcohol, stearyl alcohol, beeswax, sodium lauryl sulfate in an about 30% solution, citric acid, lanolin oil, propylene glycol, tetrasodium EDTA, cod liver oil, butylated hydroxytoluene, methylparaben, and propylparaben are provided. In another aspect, formulations of allantoin comprising about 9.0% of allantoin, water, cetyl alcohol, stearyl alcohol, beeswax, sodium lauryl sulfate in a about 30% solution, citric acid, lanolin oil, propylene glycol, tetrasodium EDTA, cod liver oil, butylated hydroxytoluene, methylparaben, and propylparaben are provided.

In another aspect, embodiments describe methods of treatment of inflammatory skin conditions comprising administrating a composition comprising from about 2.5% to about 15% allantoin and a pharmaceutically acceptable excipient. In some embodiments, the amount of allantoin is not 1.5% by weight or less of the composition. In some embodiments, the amount of allantoin is not 2.0% by weight or less of the composition. In embodiments, the composition further comprises an emollient, an emulsifier, a solvent, a pH modifier, a solubilizing agent, an antioxidant, a preservative, a chelating agent, an additive, a viscosity agent or a combination thereof. In some embodiments, the formulation comprises allantoin, water, cetyl alcohol, stearyl alcohol, beeswax, sodium lauryl sulfate in an about 30% solution, citric acid, lanolin oil, propylene glycol, cod liver oil, butylated hydroxytoluene, methylparaben, propylparaben or a combination thereof. In some embodiments, the formulation comprises allantoin in an amount from about 2.5% to about 15%, water in an amount from about 40% to about 90%; cetyl alcohol in an amount from about 0.5% to about 15%; stearyl alcohol in an amount from about 1% to about 3%; beeswax in an amount from about 1.5% to about 3%; sodium lauryl sulfate in a 30% solution in an amount from about 1.5% to about 3%; citric acid in an amount from about 0.5% to about 0.2%; lanolin oil in an amount from about 5% to about 15%; propylene glycol in an amount from about 2% to about 8%; cod liver oil in an amount from about 0.05% to about 5%; butylated hydroxytoluene in an amount from about 0.05% to about 1%; methylparaben in an amount from about 0.05% to about 0.5%; propylparaben in an amount from about 0.05% to about 0.5% by weight of the formulation or a combination thereof. In embodiments, the formulation optionally includes tetrasodium EDTA. In embodiments, the tetrasodium EDTA may be present in an amount from about 0.05% to about 0.5% by weight of the formulation. In embodiments, the formulation optionally includes a fragrance. In some embodiments, allantoin may be present in an amount from about 1.5% to about 15%, from about 2.0% to about 15%, from about 2.5% to about 15% or from about 3.0% to about 15% by weight of the formulation.

In another aspect, embodiments describe methods of treatment of inflammatory skin conditions comprising administering a composition comprising about 3.0% allantoin and a pharmaceutical excipient. In another aspect, embodiments describe methods of treatment of inflammatory skin conditions comprising administering a composition comprising about 6.0% allantoin and a pharmaceutical excipient. In another aspect, embodiments describe methods of treatment of inflammatory skin conditions comprising administering a composition comprising about 9.0% allantoin and a pharmaceutical excipient.

In some aspects, the inflammatory skin condition may be characterized by ulceration, inflammation, or blistering of the skin. In some embodiments, the inflammatory skin condition may be characterized by a genetic component, an autoimmune component, a circulatory component or combinations thereof. In some embodiments, the inflammatory skin condition may be selected from a group consisting of cutaneous porphyria, sclerodema, epidermolysis bulosa, psoriasis, decubitus ulcers, pressure ulcers, diabetic ulcers, venous stasis ulcers, sickle cell ulcers, ulcers caused by burns, eczema, urticaria, atopic dermatitis, dermatitis herpetiform, contact dermatitis, arthritis, gout, lupus erythematosus, acne, alopecia, carcinomas, psoriasis, rosacea, miliaria, inflammation due to skin infections, post-operative care of incisions, post-operative inflammation, inflammation following radiation treatment, inflammation due to dry, cracked or aged skin, skin lines, a combination thereof and a symptom thereof. In some embodiments, the symptom may be selected from pain, inflammation, itching, scarring, milia, skin thickening, redness, or a combination thereof.

In another aspect, embodiments describe methods of treatment of Epidermolysis bullosa comprising the topical administration of an about 3.0% allantoin containing composition.

In another aspect, embodiments describe methods of treatment of Epidermolysis bullosa comprising the topical administration of an about 6.0% allantoin containing composition.

In another aspect, embodiments describe methods of treatment of Epidermolysis bullosa comprising the topical administration of an about 9.0% allantoin containing composition.

In another aspect, embodiments describe methods of treatment of psoriasis comprising the topical administration of an about 3.0% allantoin containing composition.

In another aspect, embodiments describe methods of treatment of psoriasis comprising the topical administration of an about 6.0% allantoin containing composition.

In another aspect, embodiments describe methods of treatment of psoriasis comprising the topical administration of an about 9.0% allantoin containing composition.

In another aspect, embodiments describe methods of treatment of diabetic ulcers comprising the topical administration of an about 3.0% allantoin containing composition.

In another aspect, embodiments describe methods of treatment of diabetic ulcers comprising the topical administration of an about 6.0% allantoin containing composition.

In another aspect, embodiments describe methods of treatment of diabetic ulcers comprising the topical administration of an about 9.0% allantoin containing composition.

In another aspect, embodiments describe methods of treatment of atopic dermatitis comprising the topical administration of an about 3.0% allantoin containing composition.

In another aspect, embodiments describe methods of treatment of atopic dermatitis comprising the topical administration of an about 6.0% allantoin containing composition.

In another aspect, embodiments describe methods of treatment of atopic dermatitis comprising the topical administration of an about 9.0% allantoin containing composition.

These and other features provided by the present disclosure are set forth herein.

DESCRIPTION OF DRAWINGS

For a fuller understanding of the nature and advantages of the present invention, reference should be had to the following detailed description taken in connection with the accompanying drawings, in which:

FIG. 1 illustrates exemplary formulations of allantoin according to embodiments disclosed herein.

FIG. 3 includes summary tables detailing percutaneous absorption through various barriers over 48 hours from a single application of different formulations of allantoin.

FIG. 4 is a summary graph detailing percutaneous absorption through various barriers over 48 hours from a single application of different formulations of allantoin.

FIG. 7 includes tables detailing the results of membrane release of different formulations of allantoin through a porous membrane.

FIG. 9 includes tables of the results for percutaneous absorption of different formulations of allantoin through abraded and unabraded porcine cadaver skin.

FIG. 10 is a graph summarizing the percutaneous absorption of different formulations of allantoin through full thickness human cadaver skin.

FIG. 11 includes tables detailing results for percutaneous absorption of different formulations of allantoin through full thickness human cadaver skin.

FIG. 13 includes tables detailing results for percutaneous absorption of different formulations of allantoin through the isolated dermis layer from human cadaver skin.

FIG. 15 includes tables detailing results for percutaneous absorption of 9% allantoin through the isolated dermis layer from human cadaver skin.

DETAILED DESCRIPTION

Figure 2:
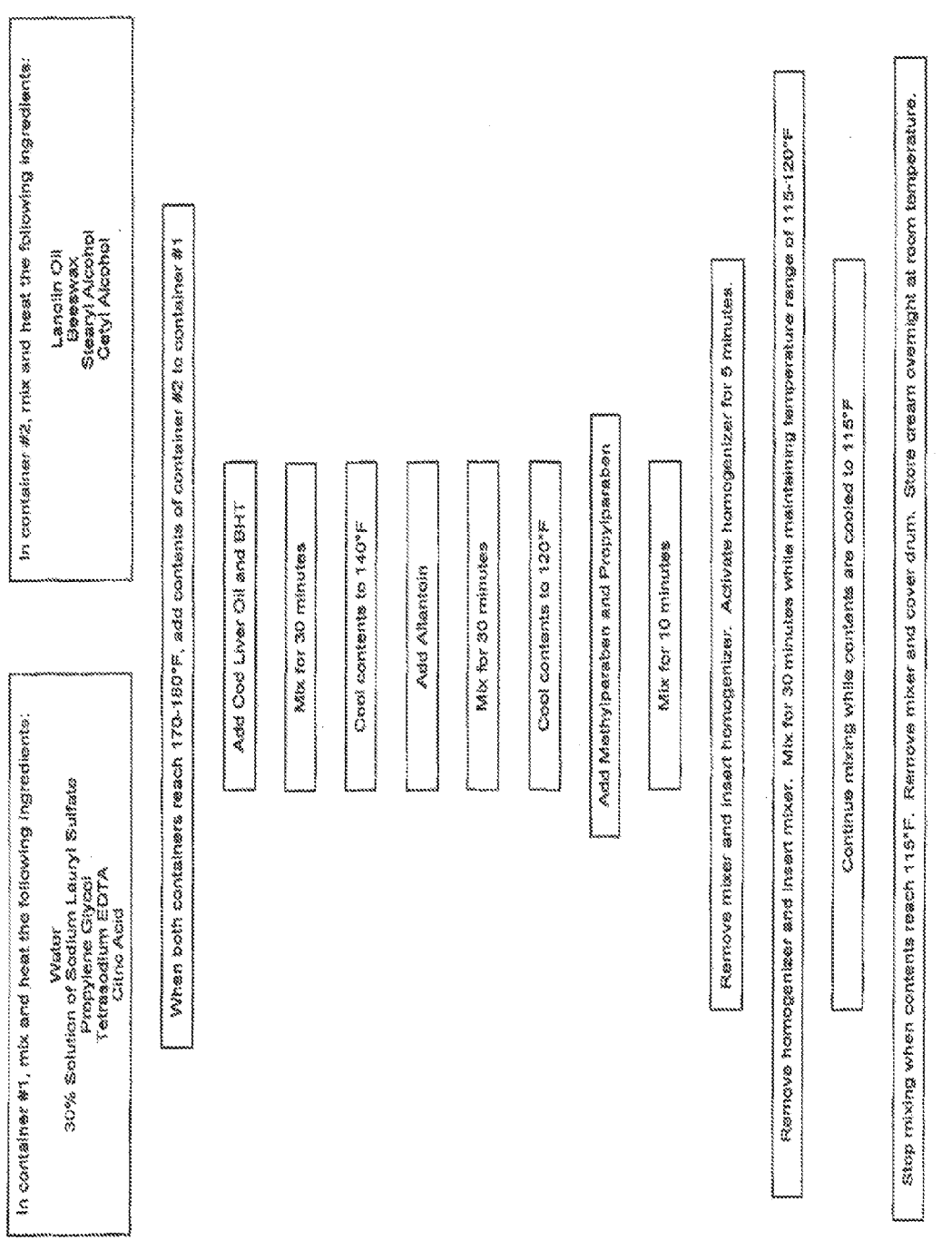
FIG. 2 illustrates an exemplary embodiment of a method of manufacture of pharmaceutical compositions disclosed herein.
Figure 5:
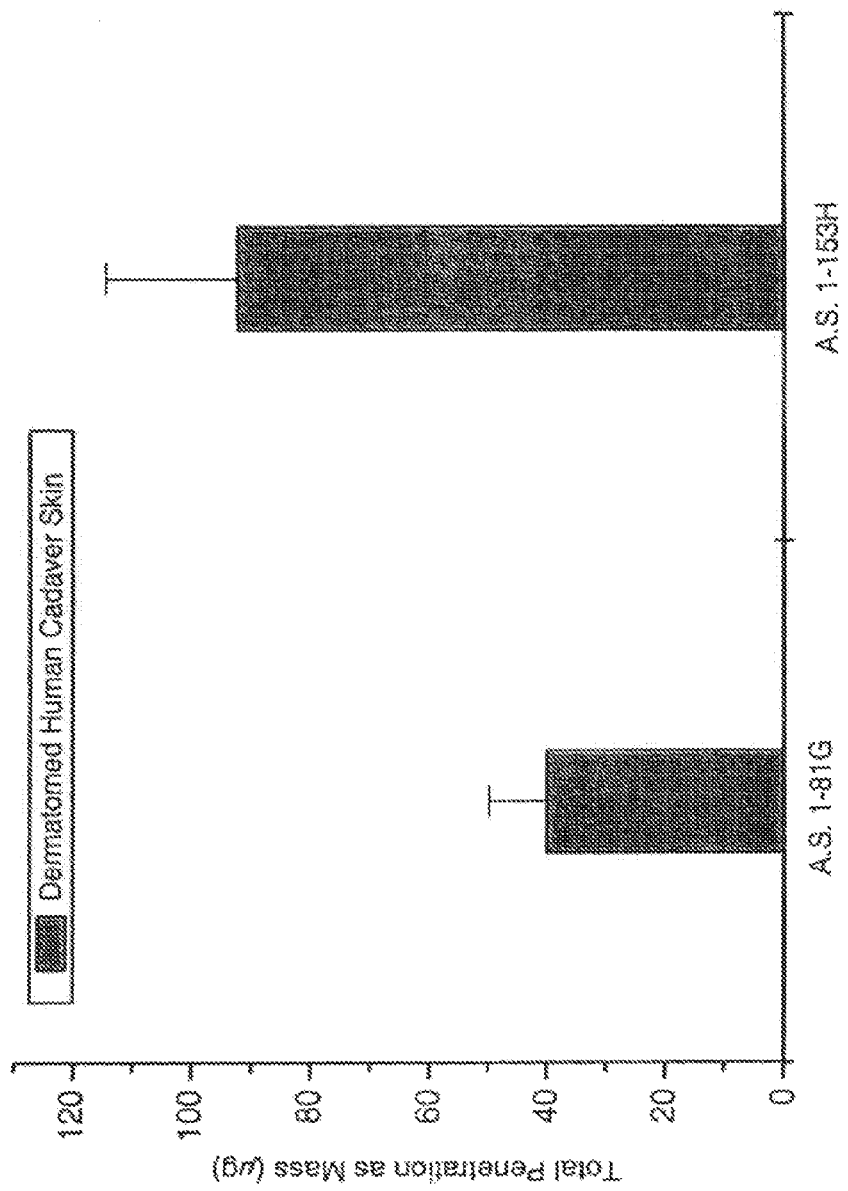
FIG. 5 is a summary graph detailing percutaneous absorption through dermatomed human cadaver skin over 48 hours from a single application of formulations of 9% allantoin.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "fibroblast" is a reference to one or more fibroblasts and equivalents thereof known to those skilled in the art, and so forth.

As used herein, the term "about" means plus or minus 10% of the numerical value of the number with which it is being used. In other aspects, the term "about" means plus or minus 1% of the numerical value of the number with which it is being used. Therefore, about 50% means in the range of 45%-55% or 49.5%-50.5% as described herein.

As used herein, the term "consists of" or "consisting of" means that the formulation includes only the elements, steps, or ingredients specifically recited in the particular claimed embodiment or claim.

As used herein, the term "consisting essentially of" or "consists essentially of" means that the only active pharmaceutical ingredient in the formulation or method that treats the specified condition (e.g. Epidermolysis bullosa, psoriasis, atopic dermatitis, diabetic ulcers or the like) is the specifically recited therapeutic in the particular embodiment or claim.

The term "inhibiting" includes the administration of a compound of the present invention to prevent the onset of the symptoms, alleviating the symptoms, or eliminating the disease, condition or disorder.

By "pharmaceutically acceptable", it is meant the carrier, diluent or excipient must be compatible with the other ingredients of the formulation and not deleterious to the recipient thereof.

As used herein, "room temperature" means an indoor temperature of from about 20° C. to about 25° C. (68 to 77° F.).

Unless otherwise indicated, the term "skin" means that outer integument or covering of the body, consisting of the dermis and the epidermis and resting upon subcutaneous tissue.

The term "improves" is used to convey that the present invention changes either the appearance, form, characteristics and/or the physical attributes of the tissue to which it is being provided, applied or administered. The change in form may be demonstrated by any of the following alone or in combination: enhanced appearance of the skin; decreased inflammation of the skin, prevention of inflammation or blisters, decreased spread of blisters, decreased ulceration of the skin, decreased redness, reduction of scarring, reduction in lesions, healing of blisters, reduced skin thickening, closure of wounds and lesions, a reduction in symptoms including, but not limited to, pain, inflammation, itching, milia or other symptoms associated with inflammatory disease or the like.

As used herein, the term "sole active ingredient" means that the active ingredient or active compound (identified as such) is the only effective therapeutic in the formulation to treat the disease or disorder. In some embodiments, allantoin is the sole active ingredient in formulation for the treatment of inflammatory skin diseases such as Epidermolysis bullosa, psoriasis, atopic dermatitis, diabetic ulcers, or the like. As an example, in embodiments where a formulation used for the treatment of psoriasis contains allantoin as the sole active ingredient, the formulation does not contain another active ingredient, such as, for example, coal tar.

As used herein, the term "therapeutic" means an agent utilized to treat, combat, ameliorate, prevent or improve an unwanted condition or disease of a patient. In part, embodiments of the present invention are directed to the treatment of various skin conditions or disorders, such as inflammatory skin conditions or disorders.

A "therapeutically effective amount" or "effective amount" of a composition is a predetermined amount calculated to achieve the desired effect, i.e., to enhance appearance of skin, to alleviate inflammation or blisters, or to prevent the skin condition from worsening. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects.

For example, in some aspects, the invention is directed to a method of treating a disease using a pharmaceutical composition comprising a compound, as defined above, and a pharmaceutically acceptable carrier or diluent, or an effective amount of a pharmaceutical composition comprising a compound as defined above.

Compounds. The structure of allantoin is:

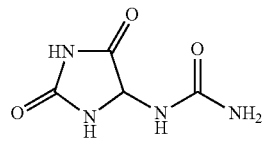 [SMILES: NC(=O)NC1NC(=O)NC1=O]

Encompassed within this disclosure is all forms of allantoin, or a salt thereof, including, but not limited to, crystals, polymorphs, clathrates, solvates, hydrates, amorphous forms, co-crystals, and anhydrous forms. As used herein, "allantoin"

includes salts thereof (as described below), crystals, polymorphs, clathrates, solvates, hydrates, amorphous forms, co-crystals, and anhydrous forms unless otherwise specified.

Embodiments of the present disclosure also relate to the salts of allantoin. The acids which are used to prepare the salts of the aforementioned compound are those which form non-toxic salts, i.e., salts containing pharmacologically acceptable anions, such as the hydrochloride, acetate, trifluoroacetic acid, tosylate, picrate, hydrobromide, hydroiodide, nitrate, sulfate, bisulfate, phosphate, acid phosphate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate salts.

Inflammatory skin disease, particularly chronic inflammatory skin disease, is still a major source of morbidity. Such inflammatory skin diseases are disfiguring and cause severe physical and psychological harm to patients, disrupting their quality of life substantially. Inflammatory skin diseases may be selected from genetic inflammatory skin diseases, circulatory inflammatory skin diseases and auto-immune inflammatory skin diseases. Such diseases include cutaneous porphyria, sclerodema, epidermolysis bulosa, psoriasis, decubitus ulcers, pressure ulcers, diabetic ulcers, venous stasis ulcers, sickle cell ulcers, and ulcers caused by bums, as well as other conditions affecting the skin and having an inflammatory component such as eczema, urticaria, atopic dermatitis, dermatitis herpetiform, contact dermatitis, arthritis, gout, and lupus erythematosus. Other skin conditions having an inflammatory component for which improved treatments are needed include acne, alopecia, carcinomas, psoriasis, rosacea, miliaria, skin infections, post-operative care of incisions, post-operative skin care following any variety of plastic surgery operations, skin care following radiation treatment, care of dry, cracked or aged skin and skin lines. Such skin diseases tend to be chronic and difficult to treat, particularly in patients with poor circulation or other underlying disease states. Symptoms of such diseases may include, without limitation, pain, inflammation, itching, milia, blisters, ulceration, redness, scarring or the like.

Among the most difficult to treat of these diseases is epidermolysis bullosa. Epidermolysis bullosa (EB) is a rare genetic disorder caused by a mutation in the keratin gene. The disorder is characterized by the presence of extremely fragile skin, severe inflammation, recurrent blister formation and scarring, resulting from minor mechanical friction or trauma. Epidermolysis bullosa is difficult to treat by conventional means.

Many allantoin compositions are prepared as emulsions, particularly oil-in-water emulsions. One emulsifier system used with such compositions is a combination of sodium lauryl sulfate and beeswax. Although solutions of sodium lauryl sulfate are alkaline with an approximate pH of 9.5, the simultaneous use of beeswax with its organic acids produces a complex neutralized system with a pH of about 6.8 to about 7.5. However, in such a system with a pH range of 6.8 to 7.5, allantoin degrades significantly with time and in accelerated stability tests at 40° C. Because preparations designed for application to the skin are typically stored by users at room temperature, and room temperatures can fluctuate with climactic conditions, such a degree of stability is undesirable. Therefore, there is a need for an oil-in-water emulsified composition containing allantoin in which the stability of allantoin is increased.

In general, embodiments herein describe a method of treating inflammatory skin conditions or diseases comprising applying to the skin an allantoin comprising composition in a therapeutically effective amount. It was unexpectedly found that stabilized oil-in-water emulsions containing allantoin optionally plus other pharmaceutically acceptable ingredients as described herein provide a high degree of relief for inflammatory skin conditions characterized by ulceration, inflammation, or blistering of skin. Such skin conditions may include, without limitation, cutaneous porphyria, sclerodema, epidermolysis bullosa, psoriasis, decubitus ulcers, pressure ulcers, diabetic ulcers, venous stasis ulcers, sickle cell ulcers, ulcers caused by bums, eczema, urticaria, atopic dermatitis, dermatitis herpetiform, contact dermatitis, arthritis, gout, lupus erythematosus, acne, alopecia, carcinomas, psoriasis, rosacea, miliaria, skin infections, post-operative care of incisions, post-operative skin care following any variety of plastic surgery operations, skin care following radiation treatment, care of dry, cracked or aged skin and skin lines as well as other conditions affecting the skin and having an inflammatory component. Administration of formulations of allantoin described in embodiments herein may cause a reduction in symptoms of such diseases such as, without limitation, pain, scarring, inflammation, redness, milia, itching, skin thickening, blisters, or other symptoms associated with inflammatory disease. In some embodiments, inflammatory skin disease may comprise epidermolysis bullosa, psoriasis, atopic dermatitis, and diabetic ulcers. The allantoin-containing composition comprises an oil-in-water emulsion as may be described below.

Furthermore, formulations of allantoin in embodiments described herein may impart long lasting stability at room temperature (where refrigeration is not needed) to the formulation. In some embodiments, the formulation may be stable for about 4 to about 10 years, for about 4 to about 8 years, for about 4 to about 7 years, for about 4 to about 6 years, for about 5 to about 10, for about 5 to about 8 years, for about 5 to about 7 years, for about 5 to about 6 years, for about 6 to about 10 years, for about 6 to about 8 years, or for about 6 to about 7 years. In some embodiments, stability may include, without limitation, physical stability, chemical stability, resistance to microbial agents or combinations thereof. In some embodiments, stability refers to a stability of allantoin. In some embodiments, stability refers to a period where there is no degradation of allantoin at room temperature. In some embodiments, stability refers to a period where there may be about 1% or less degradation of allantoin at room temperature. In some embodiments, stability refers to a period where there is no decrease in concentration. In some embodiments, stability refers to a period where there is less than about 1% decrease in concentration. In some embodiments, stability refers to a period of resistance to microbiological growth at room temperature. In some embodiments, stability refers to a period where the formulation falls within the normal bioburden ranges for said formulation at room temperature. In some embodiments, the formulations of allantoin in embodiments described herein may impart better absorption of the active pharmaceutical across a skin barrier. In some embodiments, the skin barrier comprises intact skin. In some embodiments, the formulations of allantoin in embodiments described herein may deliver more allantoin across intact skin barrier than formulations of prior art.

Embodiments of the present disclosure relate to formulations of allantoin and methods of treatment of inflammatory skin conditions. In some embodiments, the formulation comprises about 0.5% or more of allantoin and a pharmaceutically acceptable excipient. In some embodiments, the formulation consists essentially of about 0.5% or more of allantoin and a pharmaceutically acceptable excipient. In some embodiments, the formulation consists of about 0.5% or more of allantoin and a pharmaceutically acceptable excipient. In some embodiments, the formulation comprises about 1.5% or more of allantoin and a pharmaceutically acceptable excipient. In some embodiments, the formulation consists essentially of about 1.5% or more of allantoin and a pharmaceutically acceptable excipient. In some embodiments, the formulation consists of about 1.5% or more of allantoin and a pharmaceutically acceptable excipient. In some embodiments, the formulation comprises about 2.0% or more of allantoin and a pharmaceutically acceptable excipient. In some embodiments, the formulation consists essentially of about 2.0% or more of allantoin and a pharmaceutically acceptable excipient. In some embodiments, the formulation consists of about 2.0% or more of allantoin and a pharmaceutically acceptable excipient. In some embodiments, the formulation comprises about 2.5% or more of allantoin and a pharmaceutically acceptable excipient. In some embodiments, the formulation consists essentially of about 2.5% or more of allantoin and a pharmaceutically acceptable excipient. In some embodiments, the formulation consists of about 2.5% or more of allantoin and a pharmaceutically acceptable excipient. In some embodiments, the formulation comprises about 3.0% or more of allantoin and a pharmaceutically acceptable excipient. In some embodiments, the formulation consists essentially of about 3.0% or more of allantoin and a pharmaceutically acceptable excipient. In some embodiments, the formulation consists of about 3.0% or more of allantoin and a pharmaceutically acceptable excipient.

Embodiments describe a composition comprising allantoin in an amount from about 0.5% to about 15% by weight and a pharmaceutically acceptable excipient. In some embodiments, the composition comprises allantoin in an amount from about 1.5% to about 15% by weight and a pharmaceutically acceptable excipient. In some embodiments, the composition comprises allantoin in an amount from about 2.0% to about 15% by weight and a pharmaceutically acceptable excipient. In some embodiments, the composition comprises allantoin in an amount from about 2.5% to about 15% by weight and a pharmaceutically acceptable excipient. In some embodiments, the composition comprises allantoin in an amount from about 3.0% to about 15% by weight and a pharmaceutically acceptable excipient. In some embodiments, the composition comprises allantoin in an amount from about 3.0% to about 10% by weight and a pharmaceutically acceptable excipient. In some embodiments, the composition comprises allantoin in an amount from about 3.0% to about 9.0% by weight and a pharmaceutically acceptable excipient. In some embodiments, the composition comprises allantoin in an amount from about 3.0% to about 6.0% by weight and a pharmaceutically acceptable excipient. In some embodiments, the composition comprises allantoin in an amount from about 6.0% to about 15.0% by weight and a pharmaceutically acceptable excipient. In some embodiments, the composition comprises allantoin in an amount from about 6.0% to about 10.0% by weight and a pharmaceutically acceptable excipient. In some embodiments, the composition comprises allantoin in an amount from about 6.0% to about 9.0% by weight and a pharmaceutically acceptable excipient.

Embodiments describe a composition consisting essentially of allantoin in an amount from about 0.5% to about 15% by weight and a pharmaceutically acceptable excipient. In some embodiments, the composition consists essentially of allantoin in an amount from about 1.5% to about 15% by weight and a pharmaceutically acceptable excipient. In some embodiments, the composition consists essentially of allantoin in an amount from about 2.0% to about 15% by weight and a pharmaceutically acceptable excipient. In some embodiments, the composition consists essentially of allantoin in an amount from about 2.5% to about 15% by weight and a pharmaceutically acceptable excipient. In some embodiments, the composition consists essentially of allantoin in an amount from about 3.0% to about 15% by weight and a pharmaceutically acceptable excipient. In some embodiments, the composition consists essentially of allantoin in an amount from about 3.0% to about 10% by weight and a pharmaceutically acceptable excipient. In some embodiments, the composition consists essentially of allantoin in an amount from about 3.0% to about 9.0% by weight and a pharmaceutically acceptable excipient. In some embodiments, the composition consists essentially of allantoin in an amount from about 3.0% to about 6.0% by weight and a pharmaceutically acceptable excipient. In some embodiments, the composition consists essentially of allantoin in an amount from about 6.0% to about 15.0% by weight and a pharmaceutically acceptable excipient. In some embodiments, the composition consists essentially of allantoin in an amount from about 6.0% to about 10.0% by weight and a pharmaceutically acceptable excipient. In some embodiments, the composition consists essentially of allantoin in an amount from about 6.0% to about 9.0% by weight and a pharmaceutically acceptable excipient.

Embodiments describe a composition consisting of allantoin in an amount from about 0.5% to about 15% by weight and a pharmaceutically acceptable excipient. In some embodiments, the composition consists of allantoin in an amount from about 1.5% to about 15% by weight and a pharmaceutically acceptable excipient. In some embodiments, the composition consists of allantoin in an amount from about 2.0% to about 15% by weight and a pharmaceutically acceptable excipient. In some embodiments, the composition consists of allantoin in an amount from about 2.5% to about 15% by weight and a pharmaceutically acceptable excipient. In some embodiments, the composition consists of allantoin in an amount from about 3.0% to about 15% by weight and a pharmaceutically acceptable excipient. In some embodiments, the composition consists of allantoin in an amount from about 3.0% to about 10% by weight and a pharmaceutically acceptable excipient. In some embodiments, the composition consists of allantoin in an amount from about 3.0% to about 9.0% by weight and a pharmaceutically acceptable excipient. In some embodiments, the composition consists of allantoin in an amount from about 3.0% to about 6.0% by weight and a pharmaceutically acceptable excipient. In some embodiments, the composition consists of allantoin in an amount from about 6.0% to about 15.0% by weight and a pharmaceutically acceptable excipient. In some embodiments, the composition consists of allantoin in an amount from about 6.0% to about 10.0% by weight and a pharmaceutically acceptable excipient. In some embodiments, the composition consists of allantoin in an amount from about 6.0% to about 9.0% by weight and a pharmaceutically acceptable excipient.

In other embodiments, the formulation comprises more than about 1.5% by weight of allantoin, but not 1.5% or less of allantoin, and a pharmaceutically acceptable excipient. In some embodiments, the formulation comprises about 2.0% by weight or more of allantoin, but not 1.5% or less of allantoin, and a pharmaceutically acceptable excipient. In some embodiments, the formulation comprises about 2.5% by weight or more of allantoin, but not 1.5% or less of allantoin, and a pharmaceutically acceptable excipient. In some embodiments, the formulation comprises about 2.5% by weight or more of allantoin, but not less than 2.0% of allantoin, and a pharmaceutically acceptable excipient. In some embodiments, the formulation comprises about 3.0% by weight or more of allantoin, but not less than 2.5% of allantoin, and a pharmaceutically acceptable excipient. In some embodiments, the formulation comprises about 3.0% by weight or more of allantoin, but not less than 2.0% of allantoin, and a pharmaceutically acceptable excipient. In other embodiments, the formulation comprises about 3.0% by weight or more of allantoin, but not 1.5% or less of allantoin and a pharmaceutically acceptable excipient. In other embodiments, the formulation consists essentially of more than about 1.5% by weight of allantoin, but not 1.5% or less of allantoin, and a pharmaceutically acceptable excipient. In some embodiments, the formulation consists essentially of about 2.0% by weight or more of allantoin, but not 1.5% or less of allantoin, and a pharmaceutically acceptable excipient. In some embodiments, the formulation consists essentially of about 2.5% by weight or more of allantoin, but not 1.5% or less of allantoin, and a pharmaceutically acceptable excipient. In some embodiments, the formulation consists essentially of about 2.5% by weight or more of allantoin, but not less than 2.0% of allantoin, and a pharmaceutically acceptable excipient. In other embodiments, the formulation consists essentially of about 3.0% by weight or more of allantoin, but not less than 2.5% of allantoin, and a pharmaceutically acceptable excipient. In some embodiments, the formulation consists essentially of about 3.0% by weight or more of allantoin, but not less than 2.0% of allantoin and a pharmaceutically acceptable excipient. In other embodiments, the formulation consists essentially of about 3.0% by weight or more of allantoin but not 1.5% or less of allantoin and a pharmaceutically acceptable excipient. In other embodiments, the formulation consists of more than about 1.5% by weight of allantoin, but not 1.5% or less of allantoin, and a pharmaceutically acceptable excipient. In some embodiments, the formulation consists of about 2.0% by weight or more of allantoin, but not 1.5% or less of allantoin, and a pharmaceutically acceptable excipient. In some embodiments, the formulation consists of about 2.5% by weight or more of allantoin, but not 1.5% or less of allantoin, and a pharmaceutically acceptable excipient. In some embodiments, the formulation consists of about 2.5% by weight or more of allantoin, but not less than 2.0% of allantoin, and a pharmaceutically acceptable excipient. In some embodiments, the formulation consists of about 3.0% by weight or more of allantoin but not less than 2.5% of allantoin, and a pharmaceutically acceptable excipient. In some embodiments, the formulation consists of about 3.0% by weight or more of allantoin, but not less than 2.0% of allantoin, and a pharmaceutically acceptable excipient. In other embodiments, the formulation consists of about 3.0% by weight or more of allantoin, but not 1.5% or less of allantoin, and a pharmaceutically acceptable excipient.

Embodiments herein describe formulations of allantoin comprising an oil-in-water emulsion comprising allantoin, an emollient, an emulsifier and a solvent. In some embodiments, the formulation further comprises a pH modifier, a solubilizing agent, an antioxidant, a preservative, a chelating agent, an additive, a viscosity agent or a combination thereof. In some embodiments, the formulation comprises allantoin, an emollient, an emulsifier, a pH modifier, a solubilizing agent, an antioxidant, a preservative and a solvent. In some embodiments, the formulation consists essentially of allantoin, an emollient, an emulsifier, a pH modifier, a solubilizing agent, an antioxidant, a preservative and a solvent. In some embodiments, the formulation consists of allantoin, an emollient, an emulsifier, a pH modifier, a solubilizing agent, an antioxidant, a preservative and a solvent.

The formulations of various embodiments may include any number of additional components such as, for example, preservatives, emulsion stabilizers, pH adjusters, chelating agents, viscosity modifiers, anti-oxidants, surfactants, emollients, opacifying agents, skin conditioners, buffers, fragrances, and combinations thereof. In some embodiments, such additional components may provide a dual purpose. For example, certain surfactants may also act as emulsifiers, certain emollients may also act as viscosity modifiers, and certain buffering agents may also act as chelating agents.

In particular, embodiments of the present disclosure relate to formulations of allantoin comprising an oil-in-water emulsion comprising allantoin; a solvent; an emollient such as, without limitation, lanolin oil, cod liver oil or an alcohol used as a thickening agent; an emulsifier such as, without limitation, sodium laurate sulfate or a white wax; an antioxidant such as, without limitation, butylated hydroxytoluene; a preservative such as, without limitation, methylparaben or propylparaben; a pH modifier such as, without limitation, citric acid or lactic acid; and a solubilizing agent such as, without limitation, glycerin or propylene glycol. In some embodiments, the formulation may further comprise a fragrance, an herbal extract, a viscosity agent such as, without limitation, cetyl alcohol or stearyl alcohol, a chelating agent such as, without limitation, tetrasodium EDTA, or a combination thereof. In some embodiments, the formulation of allantoin comprises any formulation disclosed in FIG. 1. In some embodiments, the formulation of allantoin consists essentially of any formulation disclosed in FIG. 1. In some embodiments, the formulation of allantoin consists of any formulation disclosed in FIG. 1. In some embodiments, the formulation of allantoin comprises a formulation selected from the group consisting of 1-206A, 1-192A, 1-196A and 1-204A as shown in FIG. 1. In some embodiments, the formulation of allantoin consists essentially of a formulation selected from the group consisting of 1-206A, 1-192A, 1-196A and 1-204A as shown in FIG. 1. In some embodiments, the formulation of allantoin consists of a formulation selected from the group consisting of 1-206A, 1-192A, 1-196A and 1-204A as shown in FIG. 1. In an embodiment, a formulation of allantoin comprises an oil-in-water emulsion comprising allantoin, water, cetyl alcohol, stearyl alcohol, beeswax, sodium lauryl sulfate in a 30% solution, citric acid, lanolin oil, propylene glycol, tetrasodium EDTA, cod liver oil, butylated hydroxytoluene, methylparaben, and propylparaben.

In some embodiments, the formulation may include an emulsifying agent, or emulsifier. In embodiments, the emulsifier may be, for example, sodium lauryl sulfate, white waxes such as beeswax or paraffin wax, sesquioleates such as sorbitan sesquioleate or polyglyceryl-2-sesquioleate, ethoxylated esters of derivatives of natural oils such as the polyethoxylated ester of hydrogenated castor oil, silicone emulsifiers such as silicone polyols, anionic emulsifiers, fatty acid soaps such as potassium stearate and fatty acid sulphates like sodium cetostearyl sulphate, ethoxylated fatty alcohols, sorbitan esters, ethoxylated sorbitan esters, ethoxylated fatty acid esters such as ethoxylated stearates, ethoxylated mono, di-, and triglycerides, non-ionic self-emulsifying waxes, ethoxylated fatty acids, methylglucose esters such as polyglycerol-3 methyl glucose distearate, and combinations thereof. Various emulsions suitable for embodiments described herein and methods for preparing such emulsions are well known in the art and are described in, for example, Remington's Pharmaceutical Sciences, Mack Publishing Co., Easton, Pa., USA, which is hereby incorporated by reference in its entirety. In some embodiments, the formulation may include an emulsifier in an amount from about 1% to about 15%, and in other embodiments, the formulation may include from about 1% to about 10%, or from about 1% to about 5% emulsifier. If more than one emulsifier is used, the formulation may include from about 1% to about 5% or from about 1.5% to about 3% by weight of the formulation of each emulsifier.

In some embodiments, the formulations described herein may include one or more surfactants. Such embodiments are not limited by type of surfactant used; for example, in some embodiments, the one or more surfactants may be anionic surfactants such as alkyl sulfates, alkylether sulfates, alkylsulfonates, alkylaryl sulfonates, alkyl succinates, alkyl sulfosuccinates, N-alkoylsarcosinates, acyl taurates, acyl isethionates, alkyl phosphates, alkyl ether phosphates, alkyl ether carboxylates, α-olefinsulfonates, and the alkali metal and alkaline earth metal salts and ammonium and triethanolamine salts thereof. Such alkyl ether sulfates, alkyl ether phosphates and alkyl ether carboxylates can have between 1 and 10 ethylene oxide or propylene oxide units, and in some embodiments, 1 to 3 ethylene oxide units, per molecule. More specific examples include, but are not limited to, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzene sulfonate, triethanolamine dodecylbenzenesulfonate. In other embodiments, the one or more surfactants may be amphoteric surfactants such as, for example, alkylbetaines, alkylamidopropylbetaines, alkylsulfobetaines, alkylglycinates, alkylcarboxyglycinates, alkylamphoacetates or α-propionates, alkylamphodiacetates or α-dipropionates, and more specifically, cocodimethylsulfopropylbetaine, lauryl betaine, cocamidopropylbetaine or sodium cocamphopropionate.

In certain embodiments, the one or more surfactants may be non-ionic surfactants such as, for example, the reaction products of aliphatic alcohols or alkylphenols having 6 to 20 carbon atoms in a linear or branched alkyl chain with ethylene oxide and/or propylene oxide where the alkylene oxide may be from about 6 moles to about 60 moles per mole of alcohol. In particular embodiments, non-ionic surfactants may include alkylamine oxides, mono- and dialkylalkanolamides, fatty acid esters of polyethylenenglycols, ethoxylated fatty acids amides, saturated fatty acid alcohols reacted with ethylene oxide, alkyl polyglycosides, and sorbitan ether esters, and in some embodiments, the non-ionic surfactant may be ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceteareth-33, ceteareth-34, ceteareth-40, ceteareth-50, ceteareth-55, ceteareth-60, ceteareth-80, ceteareth-100, and the like or combinations thereof, or one or more ceteareth in combination with a fatty acid alcohol such as stearyl alcohol, oleyl alcohol, linoleyl alcohol, arachidyl alcohol, cetyl alcohol, and the like. The surfactant of various embodiments may make up from about 0.1% to about 20% by weight of the formulation and in some embodiments, from about 0.5% to about 20% by weight of the formulation. In embodiments in which more than one surfactant is provided in the formulation, each surfactant may be from about 0.5% to about 10% by weight of the formulation, and in some embodiments, each surfactant of the formulation may be from about 0.5% to about 6% by weight of the formulation.

In some embodiments, the formulation may comprise emollients in an amount from about 8% to about 30% by weight of the formulation. In formulations that include more than one emollient, each emollient may be provided at about 0.05% to about 15% by weight of any one emollient. Emollients are well known in the art and are listed, for example, the International Cosmetic Ingredient Dictionary, Eighth Edition, 2000, which is hereby incorporated by reference in its entirety. In certain embodiments, the emollient may be fatty esters, fatty alcohols, or combinations thereof including, but not limited to, diisopropyl adipate, oleyl alcohol, lanolin, isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, polyoxypropylene (5) poloxyethylene (20) cetyl ether (PPG-5-Ceteth-20), 2-ethylhexyl isononoate, 2-ethylhexyl stearate, $C_{12}$ to $C_{16}$ fatty alcohol, $C_{12}$ to $C_{16}$ fatty alcohol lactate, isopropyl lanolate, 2-ethyl-hexyl salicylate, and combinations thereof. In some embodiments, the one or more emollients may be a combination of fatty alcohols. In certain embodiments, the one or more emollients may be 1-hexadecanol, acetylated lanolin, behenocyl dimethicone, $C_{12-15}$ alkyl benzoate, cetearyl octanoate, cocoglycerides, dicaprylate/dicaprate dimethicone copolyol, dimethiconol, dioctyl adipate, glyceryl stearate, isocetyl alcohol, isohexadecane, isopentylcyclohexanone, isopropyl palmitate, lauryl lactate, mineral oil, methoxy peg-22/dodecyl glycol copolymer, myristyl lactate, ocryldodecyl neopentanoate, octyl cocoate, octyl palmitate, octyl stearate, octyldodecyl neopentanoate, polyglyceryl-4 isosterate, polyoxyl 40 stearate, polyoxymethylene urea, potassium sorbate, propylene glycol, propylene glycol isoceth-3 acetate, and propylene glycol myristyl ether acetate. In some embodiments, the emollient may be a high molecular weight saturated and unsaturated fatty alcohol such as, but not limited to, carbitol, lauryl alcohol, myristyl alcohol, cetyl alcohol, isocetyl alcohol, stearyl alcohol, isostearyl alcohol, hydroxystearyl alcohol, oleyl alcohol, ricinoleyl alcohol, behenyl alcohol, erucyl alcohol, 2-octyldodecanyl alcohol, cetearyl alcohol, lanolin alcohol, or the like. In particular embodiments, the emollient may be selected from cetyl alcohol, stearyl alcohol, lanolin oil, cod liver oil, or a combination thereof. In some embodiments, the formulation may comprise an emollient such as, without limitations, cetyl alcohol in an amount from about 2% to about 6%, stearyl alcohol in an amount from about 1% to about 3%, lanolin in an amount from about 5% to about 15%, cod liver oil in an amount from about 0.05% to about 5% or combinations thereof.

In some embodiments, the formulation may include one or more viscosity modifiers. In some embodiments, the formulation may comprise from about 1% to about 10% or from about 1% to about 6% of each viscosity modifier. The viscosity modifier of such embodiments may generally include a high molecular weight compound such as, for example, carboxyvinyl polymer, carboxymethyl cellulose, polyvinyl pyrrolidone, hydroxyethyl cellulose, methyl cellulose, natural gum such as gelatin and tragacanth gum, and various alcohols such as polyvinyl alcohol. In other embodiments, the viscosity modifier may include ethanol or isopropyl alcohol. In some embodiments, the viscosity modifier may be a high molecular weight saturated and unsaturated fatty alcohol such as, but not limited to, carbitol, lauryl alcohol, myristyl alcohol, cetyl alcohol, isocetyl alcohol, stearyl alcohol, isostearyl alcohol, hydroxystearyl alcohol, oleyl alcohol, ricinoleyl alcohol, behenyl alcohol, erucyl alcohol, 2-octyldodecanyl alcohol, cetearyl alcohol, lanolin alcohol, and the like, and in certain embodiments, the viscosity modifier may be cetyl alchol, stearyl alcohol or a combination thereof. In some embodiments, the formulation may comprise a viscosity modifier such as, without limitations, cetyl alcohol in an amount from about 2% to about 6%, stearyl alcohol in an amount from about 1% to about 3%, or combinations thereof.

Formulations of embodiments herein may further include a preservative. For example, preservatives useful in embodiments may include, but are not limited to, pentylene glycol, ethylene diamine tetra acetate (EDTA) and its salts, chlorhexidine and its diacetate, dihydrochloride, digluconate derivatives, 1,1,1-trichloro-2-methyl-2-propanol, parachlorometaxylenol, polyhexamethylenebiguanide hydrochloride, dehydroacetic acid, diazolidinyl urea, 2,4-dichlorobenzyl alcohol, 4,4-dimethyl-1,3-oxazolidine, formaldehyde, glutaraldehyde, dimethylidantoin, imidazolidinyl urea, 5-chloro-2-methyl-4-isothiazolin-3-one, ortho-phenylphenol, benzyl alcohol, benzoic acid and its salts, 4-hydroxybenzoic acid and its methyl-, ethyl-, propyl-, isopropyl-, butyl-, isobutyl-esters (parabens), methylparaben, propylparaben, isopropylparabens, isobutylparabens, butylparabens, ethylparaben, trichlosan, 2-phenoxyethanol, phenyl mercuric acetate, quatemium-15, methylsalicylate, salicylic acid and its salts, sorbic acid and its salts, iodopropanyl butylcarbamate, calcium sorbate, zinc pyrithione, 5-bromo-Snitro-1,3-dioxane, 2-bromo-2-nitropropane-1,3-diol, sulfites, bisulfites, and benzalkonium chloride, phenoxyethanol, 2-phenoxyethanol, chloroxylenol, diazolidinyl urea, and combinations thereof. In certain embodiments, the formulation may include a combination of methylparaben and propylparaben. Preservatives may be provided in any concentration known in the art. For example in some embodiments, the formulation may include preservatives in an amount from about 0.01% to about 3% by weight; and, in embodiments, the formulation may include from about 0.05% to about 1% or from about 0.05% to about 0.5% by weight of any one preservative.

The formulations of various embodiments may further include a chelating agent or combination of chelating agents. Examples of the chelating agents useful in various embodiments include, but are not limited to, alanine, sodium polyphosphate, sodium methaphosphate, citric acid, phosphoric acid, tartaric acid, ethylenediamine tetra acetic acid (Edetate, EDTA) and derivatives and salts thereof, dihydroxyethyl glycine, and combinations thereof. In particular embodiments, the chelating agent may be tetrasodium EDTA. The chelating agents may be provided in any effective amount. For example, in some embodiments, the formulation may include from about 0.01% to about 2% by weight chelating agent, and in other embodiments, the formulation may include from about 0.05% to about 0.5% or from about 0.05% to about 0.35% by weight chelating agent.

The formulations of certain embodiments may include one or more antioxidants. Numerous antioxidants are known in the art, and any such antioxidant may be used to prepare the formulations described herein. Examples of suitable antioxidants include, but are not limited to, amino acids such as glycine, histidine, tyrosine, trytophan and derivatives thereof, imidazoles such as urocanic acid and derivatives thereof, peptides, such as D,L-carnosine, D-carnosine, L-carnosine and derivatives thereof such as anserine, carotinoids, carotenes such as α-carotene, β-carotene, lycopene, and derivatives thereof, chlorogenic acid and derivatives thereof, lipoic acid and derivatives thereof such as dihydrlipoic acid, aurothioglycose, propylthiouracil and other thiols such as thioredoxin, glutathione, cysteine, cystine, cystamine and glycosyl, N-acetyl, methyl, ethyl, propyl, amyl, butyl, lauryl, palmitoyl, oleyl, α-linoleyl, cholesteryl and glyceryl esters and salts thereof, dilauryl thiodipropionate, distearyl thiodipropionate, thiodipropionic acid and derivatives thereof such as esters, ethers, peptides, lipids, nucleotides, nucleosides, and salts, sulfoximine compounds such as buthionine sulfoximines, homocysteine sulfoximine, buthionine sulfones, penta-, hexa-, hepta-thionine sulfoximine, unsaturated fatty acids and derivatives thereof such as α-linolenic acid, linoleic acid, oleic acid, folic acid and derivatives thereof, ubiquinone and ubiquinol and derivatives thereof, vitamin C and derivatives there of such as ascorbyl palmitate, magnesium ascorbyl phosphate, ascorbyl acetate, tocopherals and derivatives such as vitamin E acetate, vitamin A and derivatives such as vitamin A palmitate, vitamin B and derivatives thereof, coniferyl benzoate of benzoin resin, rutinic acid and derivatives thereof, α-glycosylrutin, ferulic acid, furfurylidene glucitol, carnosine, butyl hydroxytoluene, trihydroxy-butyrophenone, uric acid and derivatives thereof, mannose and derivatives thereof, superoxide dismutase, zinc and derivatives thereof such as $ZnO$, $ZnSO_4$, selenium and derivatives thereof such as selenium methionine, stilbene and derivatives thereof such as stilbene oxide, trans-stilbene oxide and the like. In some embodiments, the antioxidants may include vitamin B, nordihydroguaiaretic acid, butylated hydroxyanisole (BHA), butylated hydroxytoluene (BHT), propyl gallate, erythorbate acid, sodium erythorbate, ascorbir palmitate, and ascorbir stearate. butyl hydroxyanisole, and gallic esters, and in particular embodiments, the one or more antioxidants may include BHT. The antioxidant may be provided in any suitable amount. For example in some embodiments, one or more antioxidants may be from about 0.001% to about 3% by weight of the formulation, and in other embodiments, the one or more antioxidants may be from about 0.01% to about 1% by weight of the formulation or from about 0.05% to about 1% by weight of the formulation.

In some embodiments, the formulation may include a solubilizing agent. In embodiments, the solubilizers may be, for example, hydrochloric acid, sodium hydroxide, glycine, cyclodextrin, liquid paraffin, hydrogenated castor oil, ethanol, glycerin, propylene glycol, dilute hydrochloric acid, hydrogenated oils, purified water, physiological saline, water for injection, Macrogol 4000, Polysorbate 80, or a combination thereof. In particular embodiments, the solubilizing agent may be propylene glycol, glycerin or a combination thereof. In embodiments, the solubilizing agent comprises from about 1% to about 20%, from about 1% to about 10% or from about 2% to about 8% by weight of the formulation.

In certain embodiments, the formulation may include one or more opacifying agents. In some embodiments, components such as, for example, emollients, surfactants, and/or emulsifiers may provide sufficient opaqueness. In other embodiments, an additional opacifying agent may be provided to the formulation. Opacifying agents are well known in the art and include, but are not limited to, higher fatty alcohols such as cetyl, stearyl, cetostearyl alcohol, arachidyl and behenyl alcohols, solid esters such as cetyl palmitate, gliceryllaurate, stearamide MEA-stearate, high molecular weight fatty amides and alkanolamides and various fatty acid derivatives such as propylene glycol and polyethylene glycol esters. In other embodiments, opacifying agents may include inorganic materials such as, for example, magnesium aluminum silicate, zinc oxide, titanium dioxide and other sunblocking agents. In embodiments in which an opacifying agent is used, the opacifying agent may be provided in any amount necessary to provide the desired opaqueness. In such embodiments, the opacifying agent may generally be from about 0.01% to about 20% by weight of the formulation, and in some embodiments, the opacifying agent may be from about 0.01% to about 10% or about 0.02% to about 5% by weight of the formulation.

In some embodiments, the formulation may include one or more skin conditioners. Common skin conditioners include, for example, mineral oil, petrolatum, aliphatic alcohols, lanolin and its derivatives, fatty acids, glycol fatty acids, sugars, glycerin, propylene glycol, sorbitols, and polyethylene glycols, vitamins and herbal derivatives. Additional skin conditioners can be found in CTFA Cosmetic Ingredient Handbook, 1st Ed., 1988, which is hereby incorporated herein by reference in its entirety. In some embodiments, the one or more skin conditioners may include, but are not limited to, humectants, such as fructose, glucose, glycerin, propylene glycol, glycereth-26, mannitol and urea, pyrrolidone carboxylic acid, hydrolyzed lecithin, coco-betaine, cysteine hydrochloride, glutamine, polyoxypropylene (15) polyoxyethylene (PPG-15), sodium gluconate, potassium aspartate, oleyl betaine, thiamine hydrochloride, sodium laureth sulfate, sodium hyaluronate, hydrolyzed proteins, hydrolyzed keratin, amino acids, amine oxides, water-soluble derivatives of vitamins A, E and D, amino-functional silicones, ethoxylated glycerin, α-hydroxy acids and salts thereof, water-soluble fatty oil derivatives, such as PEG-24 hydrogenated lanolin, almond oil, grape seed oil and castor oil; numerous other water-soluble skin conditioners listed, and combinations thereof. In certain embodiments, the skin conditioners may include lanolin or lanolin derivatives, caprylic capric/triglyceride, diisopropyl adipate, and combinations thereof. Skin conditioners may be provided to various embodiments in any amount known in the art, and the amount of skin conditioner provided may vary depending upon the type of skin condition or combination of skin conditioners used. In general, the formulations of embodiments may include a conditioner in an amount from about 1% to about 30% by weight of the formulation or from about 1% to about 25% by weight of the formulation.

The pH of various embodiments may be of neutral to mildly acidic pH to allow for comfortable application to a subject's skin, particularly in light of the disease state or condition suffered by the subject. For example, in various embodiments, the pH of the formulations may be from about 2.5 to about 7.0, from about 4.0 to about 7.0, or from about 4.0 to about 5.5 at room temperature. In other embodiments, the pH of such formulations may be about 4.0 to about 5.0 at room temperature. Any components or combination of components known and useful in the art may be used to achieve an appropriate pH such as, for example, pH regulators including, but not limited to, lactic acid, citric acid, sodium citrate, glycolic acid, succinic acid, phosphoric acid, monosodium phosphate, disodium phosphate, oxalic acid, dl-malic acid, calcium carbonate, sodium hydroxide and sodium carbonate, sodium hydrogen carbonate, and ammonium hydrogen carbonate. In particular embodiments, the formulation may include, for example, citric acid or lactic acid as a pH modifier. In embodiments, the pH modifier may comprise from about 0.01% to about 1%, from about 0.05% to about 0.5%, from about 0.06% to about 0.15%, from about 0.06% to about 0.11%, or from about 0.06% to about 0.1% by weight of the formulation.

In embodiments, the formulation may further comprise a solvent. In some embodiments, the solvent may include one or more ingredients therein, with water being preferred in certain embodiments. Generally, the quantity of water used as a solvent may depend on the various other ingredients used. The solvent may be present in certain embodiments in a range of from about 10% to about 95% by weight, with certain embodiments including from about 40% to about 90%, from about 42% to about 87%, from about 42% to about 80%, from about 42% to about 75%, from about 42% to about 70%, or from about 42% to about 68% by weight of the formulation. The exact quantity of solvent may be dependent on the form of the product. For example, a product in lotion form may in certain preferred embodiments include more water than a product in spray form and a product in cream or butter form may include less water than a product in spray form. Deionized water is generally preferred. Other suitable solvent materials may also be used.

In embodiments, the formulation of embodiments herein may be physically and chemically stable. In some embodiments, the formulation of embodiments herein may be resistant to microbial agents for up to 4 years, up to 6 years, up to 8 years, up to 10 years, up to 12 years or up to 20 years. In some embodiments, the formulation of embodiments herein may be resistant to microbial agents for from about 4 to about 20 years, from about 4 to about 12 years, from about 4 to about 10 years, from about 4 to about 8 years, from about 4 to about 6 years, from about 6 to about 20 years, from about 6 to about 12 years, from about 6 to about 10 years, from about 6 to about 8 years, from about 8 to about 20 years, from about 8 to about 12 years, or from about 8 to about 10 years.

One embodiment relates to formulations of allantoin comprising an oil-in-water emulsion comprising about 3.0% of allantoin, water, cetyl alcohol, stearyl alcohol, beeswax, sodium lauryl sulfate in a 30% solution, citric acid, lanolin oil, propylene glycol, tetrasodium EDTA, cod liver oil, butylated hydroxytoluene, methylparaben, and propylparaben. In further embodiments, the formulation consists essentially of about 3.0% of allantoin, water, cetyl alcohol, stearyl alcohol, beeswax, sodium lauryl sulfate in a 30% solution, citric acid, lanolin oil, propylene glycol, tetrasodium EDTA, cod liver oil, butylated hydroxytoluene, methylparaben, and propylparaben. In certain embodiments, the formulation consists of about 3.0% of allantoin, water, cetyl alcohol, stearyl alcohol, beeswax, sodium lauryl sulfate in a 30% solution, citric acid, lanolin oil, propylene glycol, tetrasodium EDTA, cod liver oil, butylated hydroxytoluene, methylparaben, and propylparaben. In certain embodiments, the formulation further includes a fragrance. In some embodiments, the fragrance comprises from about 0.01% to about 5%, from about 0.01% to about 3%, from about 0.01% to about 2%, from about 0.01% to about 1% from about 0.01% to about 0.5%, from about 0.05% to about 3%, from about 0.05% to about 2%, from about 0.05% to about 1% from about 0.05% to about 0.5% by weight of the formulation. In certain embodiments, the formulation does not contain a fragrance. In embodiments, the formulation may further include an herbal extract. In certain embodiments, the formulation does not contain any herbal extracts.

In another embodiment, formulations of allantoin comprising an oil-in-water emulsion comprising about 6.0% of allantoin, water, cetyl alcohol, stearyl alcohol, beeswax, sodium lauryl sulfate in a 30% solution, citric acid, lanolin oil, propylene glycol, tetrasodium EDTA, cod liver oil, butylated hydroxytoluene, methylparaben, and propylparaben are provided. In certain embodiments, the formulation does not contain a fragrance. In certain embodiments, the formulation does not contain any herbal extracts. In further embodiments, the formulations consist essentially of about 6.0% of allantoin, water, cetyl alcohol, stearyl alcohol, beeswax, sodium lauryl sulfate in a 30% solution, citric acid, lanolin oil, propylene glycol, tetrasodium EDTA, cod liver oil, butylated hydroxytoluene, methylparaben, and propylparaben. In certain embodiments, the formulations consist of about 6.0% of allantoin, water, cetyl alcohol, stearyl alcohol, beeswax, sodium lauryl sulfate in a 30% solution, citric acid, lanolin oil, propylene glycol, tetrasodium EDTA, cod liver oil, butylated hydroxytoluene, methylparaben, and propylparaben. In certain embodiments, the formulation further includes a fragrance. In certain embodiments, the formulation does not contain a fragrance. In embodiments, the formulation may further include an herbal extract. In certain embodiments, the formulation does not contain any herbal extracts.

In another embodiment, formulations of allantoin comprising an oil-in-water emulsion comprising about 9.0% of allantoin, water, cetyl alcohol, stearyl alcohol, beeswax, sodium lauryl sulfate in a 30% solution, citric acid, lanolin oil, propylene glycol, tetrasodium EDTA, cod liver oil, butylated hydroxytoluene, methylparaben, and propylparaben are provided. In certain embodiments, the formulation does not contain a fragrance. In certain embodiments, the formulation does not contain any herbal extracts. In further embodiments, the formulation consists essentially of about 9.0% of allantoin, water, cetyl alcohol, stearyl alcohol, beeswax, sodium lauryl sulfate in a 30% solution, citric acid, lanolin oil, propylene glycol, tetrasodium EDTA, cod liver oil, butylated hydroxytoluene, methylparaben, and propylparaben. In certain embodiments, the formulation consists of about 9.0% of allantoin, water, cetyl alcohol, stearyl alcohol, beeswax, sodium lauryl sulfate in a 30% solution, citric acid, lanolin oil, propylene glycol, tetrasodium EDTA, cod liver oil, butylated hydroxytoluene, methylparaben, and propylparaben. In certain embodiments, the formulation further includes a fragrance. In certain embodiments, the formulation does not contain a fragrance. In embodiments, the formulation may further include an herbal extract. In certain embodiments, the formulation does not contain any herbal extracts.

In another embodiment, the formulation comprises about 3.0% allantoin; about 67.01% water; about 3.5% cetyl alcohol; about 1.7% stearyl alcohol; about 2.5% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; about 0.2% fragrance; and about 2.5% sodium lauryl sulfate in a 30% solution. In further embodiments, the formulations consist essentially of about 3.0% allantoin; about 67.01% water; about 3.5% cetyl alcohol; about 1.7% stearyl alcohol; about 2.5% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; about 0.2% fragrance; and about 2.5% sodium lauryl sulfate in a 30% solution. In certain embodiments, the formulations consist of about 3.0% allantoin; about 67.01% water; about 3.5% cetyl alcohol; about 1.7% stearyl alcohol; about 2.5% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; about 0.2% fragrance; and about 2.5% sodium lauryl sulfate in a 30% solution.

In another embodiment, the formulation comprises about 3.0% allantoin; about 67.41% water; about 4.2% cetyl alcohol; about 2% stearyl alcohol; about 1.9% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 1.9% sodium lauryl sulfate in a 30% solution. In further embodiments, the formulation consists essentially of about 3.0% allantoin; about 67.41% water; about 4.2% cetyl alcohol; about 2% stearyl alcohol; about 1.9% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 1.9% sodium lauryl sulfate in a 30% solution. In certain embodiments, the formulation consists of about 3.0% allantoin; about 67.41% water; about 4.2% cetyl alcohol; about 2% stearyl alcohol; about 1.9% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 1.9% sodium lauryl sulfate in a 30% solution.

In another embodiment, the formulation comprises about 3.0% allantoin; about 67.41% water; about 4.2% cetyl alcohol; about 2% stearyl alcohol; about 1.9% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 1.5% sodium lauryl sulfate in a 30% solution. In further embodiments, the formulations consist essentially of about 3.0% allantoin; about 67.41% water; about 4.2% cetyl alcohol; about 2% stearyl alcohol; about 1.9% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 1.5% sodium lauryl sulfate in a 30% solution. In certain embodiments, the formulations consist of about 3.0% allantoin; about 67.41% water; about 4.2% cetyl alcohol; about 2% stearyl alcohol; about 1.9% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 1.5% sodium lauryl sulfate in a 30% solution.

In another embodiment, the formulation comprises about 3.0% allantoin; water; cetyl alcohol; stearyl alcohol; beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 2.0% sodium lauryl sulfate in a 30% solution. In further embodiments, the formulation consists essentially of about 3.0% allantoin; water; cetyl alcohol; stearyl alcohol; beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 2.0% sodium lauryl sulfate in a 30% solution. In certain embodiments, the formulation consists of about 3.0% allantoin; water; cetyl alcohol; stearyl alcohol; beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 2.0% sodium lauryl sulfate in a 30% solution.

In another embodiment, the formulation comprises about 6.0% allantoin; about 63.98% water; about 3.23% cetyl alcohol; about 1.5% stearyl alcohol; about 2.75% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; about 0.2% fragrance; and about 2.75% sodium lauryl sulfate in a 30% solution. In further embodiments, the formulations consist essentially of about 6.0% allantoin; about 63.98% water; about 3.23% cetyl alcohol; about 1.5% stearyl alcohol; about 2.75% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; about 0.2% fragrance; and about 2.75% sodium lauryl sulfate in a 30% solution. In certain embodiments, the formulations consist of about 6.0% allantoin; about 63.98% water; about 3.23% cetyl alcohol; about 1.5% stearyl alcohol; about 2.75% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; about 0.2% fragrance; and about 2.75% sodium lauryl sulfate in a 30% solution.

In another embodiment, the formulation comprises about 6.0% allantoin; about 64.81% water; about 3.5% cetyl alcohol; about 1.5% stearyl alcohol; about 2.3% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 2.3% sodium lauryl sulfate in a 30% solution. In further embodiments, the formulations consist essentially of about 6.0% allantoin; about 64.81% water; about 3.5% cetyl alcohol; about 1.5% stearyl alcohol; about 2.3% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 2.3% sodium lauryl sulfate in a 30% solution. In certain embodiments, the formulations consist of about 6.0% allantoin; about 64.81% water; about 3.5% cetyl alcohol; about 1.5% stearyl alcohol; about 2.3% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 2.3% sodium lauryl sulfate in a 30% solution.

In another embodiment, the formulation comprises about 6.0% allantoin; about 65.11% water; about 3.6% cetyl alcohol; about 1.7% stearyl alcohol; about 2.0% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 2.0% sodium lauryl sulfate in a 30% solution. In further embodiments, the formulations consist essentially of about 6.0% allantoin; about 65.11% water; about 3.6% cetyl alcohol; about 1.7% stearyl alcohol; about 2.0% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 2.0% sodium lauryl sulfate in a 30% solution. In certain embodiments, the formulations consist of about 6.0% allantoin; about 65.11% water; about 3.6% cetyl alcohol; about 1.7% stearyl alcohol; about 2.0% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 2.0% sodium lauryl sulfate in a 30% solution.

In another embodiment, the formulation comprises about 6.0% allantoin; water; cetyl alcohol; stearyl alcohol; beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 1.5% sodium lauryl sulfate in a 30% solution. In further embodiments, the formulations consist essentially of about 6.0% allantoin; water; cetyl alcohol; stearyl alcohol; beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 1.5% sodium lauryl sulfate in a 30% solution. In certain embodiments, the formulations consist of about 6.0% allantoin; water; cetyl alcohol; stearyl alcohol; beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 1.5% sodium lauryl sulfate in a 30% solution.

In another embodiment, the formulation comprises about 9.0% allantoin; about 61.78% water; about 2.7% cetyl alcohol; about 1.2% stearyl alcohol; about 2.75% beeswax; about 0.12% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; about 0.2% fragrance; and about 2.75% sodium lauryl sulfate in a 30% solution. In further embodiments, the formulations consist essentially of about 9.0% allantoin; about 61.78% water; about 2.7% cetyl alcohol; about 1.2% stearyl alcohol; about 2.75% beeswax; about 0.12% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; about 0.2% fragrance; and about 2.75% sodium lauryl sulfate in a 30% solution. In certain embodiments, the formulations consist of about 9.0% allantoin; about 61.78% water; about 2.7% cetyl alcohol; about 1.2% stearyl alcohol; about 2.75% beeswax; about 0.12% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; about 0.2% fragrance; and about 2.75% sodium lauryl sulfate in a 30% solution.

In another embodiment, the formulation comprises about 9.0% allantoin; about 63.71% water; about 2.5% cetyl alcohol; about 1.2% stearyl alcohol; about 2.0% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 2.0% sodium lauryl sulfate in a 30% solution. In further embodiments, the formulations consist essentially of about 9.0% allantoin; about 63.71% water; about 2.5% cetyl alcohol; about 1.2% stearyl alcohol; about 2.0% beeswax; about 0.09% citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and about 2.0% sodium lauryl sulfate in a 30% solution. In certain embodiments, the formulations consist of about 9.0% allantoin; about 63.71% water; about 2.5% cetyl alcohol; about 1.2% stearyl alcohol; about 2.0% beeswax; about 0.09% citric acid; about 10.6% lanolin oil; about 5.7% propylene glycol; about 0.15% tetrasodium EDTA; about 2% cod liver oil;

about 0.5% butylated hydroxytoluene; about 0.3% methylparaben; about 0.25% propylparaben; and about 2.0% sodium lauryl sulfate in a 30% solution.

In another embodiment, the formulation comprises about 9.0% allantoin; water; cetyl alcohol; stearyl alcohol; beeswax; citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and 1.5% sodium lauryl sulfate in a 30% solution. In further embodiments, the formulations consist essentially of about 9.0% allantoin; water; cetyl alcohol; stearyl alcohol; beeswax; citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and 1.5% sodium lauryl sulfate in a 30% solution. In certain embodiments, the formulations consist of about 9.0% allantoin; water; cetyl alcohol; stearyl alcohol; beeswax; citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and 1.5% sodium lauryl sulfate in a 30% solution.

In another embodiment, the formulation comprises about 9.0% allantoin; water; cetyl alcohol; stearyl alcohol; beeswax; citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and sodium lauryl sulfate in a 30% solution. In further embodiments, the formulations consist essentially of about 9.0% allantoin; water; cetyl alcohol; stearyl alcohol; beeswax; citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and sodium lauryl sulfate in a 30% solution. In certain embodiments, the formulations consist of about 9.0% allantoin; water; cetyl alcohol; stearyl alcohol; beeswax; citric acid; about 10.6% lanolin oil; about 5.7% propylene glycol; about 0.15% tetrasodium EDTA; about 2% cod liver oil; about 0.5% butylated hydroxytoluene; about 0.3% methylparaben; about 0.25% propylparaben; and sodium lauryl sulfate in a 30% solution.

Embodiments herein are also directed to methods of treating inflammatory skin conditions comprising administering a composition comprising an oil-in-water emulsion comprising allantoin in an amount from about 0.5% to about 15% by weight and a pharmaceutically acceptable excipient. In some embodiments, the formulation of allantoin comprises an oil-in-water emulsion comprising allantoin, an emollient, an emulsifier and a solvent. In some embodiments, the formulation further comprises a pH modifier, a solubilizing agent, an antioxidant, a preservative, a chelating agent, an additive, a viscosity agent or a combination thereof. In some embodiments, the formulation comprises allantoin, an emollient, an emulsifier, a pH modifier, a solubilizing agent, an antioxidant, a preservative and a solvent. In some embodiments, the formulation consists essentially of allantoin, an emollient, an emulsifier, a pH modifier, a solubilizing agent, an antioxidant, a preservative and a solvent. In some embodiments, the formulation consists of allantoin, an emollient, an emulsifier, a pH modifier, a solubilizing agent, an antioxidant, a preservative and a solvent. In some embodiments, a method of treating inflammatory skin conditions in a patient in need thereof comprises administering a formulation comprising allantoin, a solvent, an emollient, an emulsifier, an antioxidant, a preservative, a pH modifier and a solubilizing agent, wherein the allantoin is present in an amount of about 0.5% to about 15% by weight. In some embodiments, a method of treating inflammatory skin conditions in a patient in need thereof comprises administering a formulation consisting essentially of allantoin, a solvent, an emollient, an emulsifier, an antioxidant, a preservative, a pH modifier and a solubilizing agent, wherein the allantoin is present in an amount of about 0.5% to about 15% by weight. In some embodiments, a method of treating inflammatory skin conditions in a patient in need thereof comprises administering a formulation consisting of allantoin, a solvent, an emollient, an emulsifier, an antioxidant, a preservative, a pH modifier and a solubilizing agent, wherein the allantoin is present in an amount of about 0.5% to about 15% by weight.

In another embodiment, a method of treating Epidermolysis bullosa comprises administering a formulation of allantoin comprising an oil-in-water emulsion comprising allantoin, an emollient, an emulsifier, a solvent and a pharmaceutically acceptable excipient. In some embodiments, the formulation further comprises a pH modifier, a solubilizing agent, an antioxidant, a preservative, a chelating agent, an additive, a viscosity agent or a combination thereof. In some embodiments, the formulation comprises allantoin, an emollient, an emulsifier, a pH modifier, a solubilizing agent, an antioxidant, a preservative, a solvent and a pharmaceutically acceptable excipient. In some embodiments, the formulation consists essentially of allantoin, an emollient, an emulsifier, a pH modifier, a solubilizing agent, an antioxidant, a preservative, a solvent and a pharmaceutically acceptable excipient. In some embodiments, the formulation consists of allantoin, an emollient, an emulsifier, a pH modifier, a solubilizing agent, an antioxidant, a preservative, a solvent and a pharmaceutically acceptable excipient. In some embodiments, a method of treating Epidermolysis bullosa in a patient in need thereof comprises administering a formulation comprising allantoin, a solvent, an emollient, an emulsifier, an antioxidant, a preservative, a pH modifier, a solubilizing agent and a pharmaceutically acceptable excipient, wherein the allantoin is present in an amount of about 0.5% to about 15% by weight. In some embodiments, a method of treating Epidermolysis bullosa in a patient in need thereof comprises administering a formulation consisting essentially of allantoin, a solvent, an emollient, an emulsifier, an antioxidant, a preservative, a pH modifier, a solubilizing agent and a pharmaceutically acceptable excipient, wherein the allantoin is present in an amount of about 0.5% to about 15% by weight. In some embodiments, a method of treating Epidermolysis bullosa in a patient in need thereof comprises administering a formulation consisting of allantoin, a solvent, an emollient, an emulsifier, an antioxidant, a preservative, a pH modifier, a solubilizing agent and a pharmaceutically acceptable excipient, wherein the allantoin is present in an amount of about 0.5% to about 15% by weight.

In another embodiment, a method of treating psoriasis comprises administering a formulation of allantoin comprising an oil-in-water emulsion comprising allantoin, an emollient, an emulsifier, a solvent and a pharmaceutically acceptable excipient. In some embodiments, the formulation further comprises a pH modifier, a solubilizing agent, an antioxidant, a preservative, a chelating agent, an additive, a viscosity agent or a combination thereof. In some embodiments, the formulation comprises allantoin, an emollient, an emulsifier, a pH modifier, a solubilizing agent, an antioxidant, a preservative, a solvent and a pharmaceutically acceptable excipient. In some embodiments, the formulation consists essentially of allantoin, an emulsifier, a pH modifier, a solubilizing agent, an antioxidant, a preservative, a solvent and a pharmaceutically acceptable excipient. In some embodiments, the formulation consists of allantoin, an emollient, an emulsifier, a pH modifier, a solubilizing agent, an antioxidant, a preservative, a solvent and a pharmaceutically acceptable excipient. In some embodiments, a method of treating psoriasis in a patient in need thereof comprises administering a formulation comprising allantoin, a solvent, an emollient, an emulsifier, an antioxidant, a preservative, a pH modifier, a solubilizing agent and a pharmaceutically acceptable excipient, wherein the allantoin is present in an amount of about 0.5% to about 15% by weight. In some embodiments, a method of treating psoriasis in a patient in need thereof comprises administering a formulation consisting essentially of allantoin, a solvent, an emollient, an emulsifier, an antioxidant, a preservative, a pH modifier, a solubilizing agent and a pharmaceutically acceptable excipient, wherein the allantoin is present in an amount of about 0.5% to about 15% by weight. In some embodiments, a method of treating psoriasis in a patient in need thereof comprises administering a formulation consisting of allantoin, a solvent, an emollient, an emulsifier, an antioxidant, a preservative, a pH modifier, a solubilizing agent and a pharmaceutically acceptable excipient, wherein the allantoin is present in an amount of about 0.5% to about 15% by weight. As shown in Example 11, it is believed that formulations containing above 1.5% allantoin are better able to treat psoriasis than formulations of 1.5% or below. Accordingly, embodiments herein include a method of treating psoriasis disclosed herein wherein allantoin is present an amount greater than about 1.5% to about 15%.

In another embodiment, a method of treating diabetic ulcers comprises administering a formulation of allantoin comprising an oil-in-water emulsion comprising allantoin, an emollient, an emulsifier, a solvent and a pharmaceutically acceptable excipient. In some embodiments, the formulation further comprises a pH modifier, a solubilizing agent, an antioxidant, a preservative, a chelating agent, an additive, a viscosity agent or a combination thereof. In some embodiments, the formulation comprises allantoin, an emollient, an emulsifier, a pH modifier, a solubilizing agent, an antioxidant, a preservative, a solvent and a pharmaceutically acceptable excipient. In some embodiments, the formulation consists essentially of allantoin, an emollient, an emulsifier, a pH modifier, a solubilizing agent, an antioxidant, a preservative, a solvent and a pharmaceutically acceptable excipient. In some embodiments, the formulation consists of allantoin, an emollient, an emulsifier, a pH modifier, a solubilizing agent, an antioxidant, a preservative, a solvent and a pharmaceutically acceptable excipient. In some embodiments, a method of treating diabetic ulcers in a patient in need thereof comprises administering a formulation comprising allantoin, a solvent, an emollient, an emulsifier, an antioxidant, a preservative, a pH modifier, a solubilizing agent and a pharmaceutically acceptable excipient, wherein the allantoin is present in an amount of about 0.5% to about 15% by weight. In some embodiments, a method of treating diabetic ulcers in a patient in need thereof comprises administering a formulation consisting essentially of allantoin, a solvent, an emollient, an emulsifier, an antioxidant, a preservative, a pH modifier, a solubilizing agent and a pharmaceutically acceptable excipient, wherein the allantoin is present in an amount of about 0.5% to about 15% by weight. In some embodiments, a method of treating diabetic ulcers in a patient in need thereof comprises administering a formulation consisting of allantoin, a solvent, an emollient, an emulsifier, an antioxidant, a preservative, a pH modifier, a solubilizing agent and a pharmaceutically acceptable excipient, wherein the allantoin is present in an amount of about 0.5% to about 15% by weight.

In another embodiment, a method of treating atopic dermatitis comprises administering a formulation of allantoin comprising an oil-in-water emulsion comprising allantoin, an emollient, an emulsifier, a solvent and a pharmaceutically acceptable excipient. In some embodiments, the formulation further comprises a pH modifier, a solubilizing agent, an antioxidant, a preservative, a chelating agent, an additive, a viscosity agent or a combination thereof. In some embodiments, the formulation comprises allantoin, an emollient, an emulsifier, a pH modifier, a solubilizing agent, an antioxidant, a preservative, a solvent and a pharmaceutically acceptable excipient. In some embodiments, the formulation consists essentially of allantoin, an emollient, an emulsifier, a pH modifier, a solubilizing agent, an antioxidant, a preservative, a solvent and a pharmaceutically acceptable excipient. In some embodiments, the formulation consists of allantoin, an emollient, an emulsifier, a pH modifier, a solubilizing agent, an antioxidant, a preservative, a solvent and a pharmaceutically acceptable excipient. In some embodiments, a method of treating atopic dermatitis in a patient in need thereof comprises administering a formulation comprising allantoin, a solvent, an emollient, an emulsifier, an antioxidant, a preservative, a pH modifier, a solubilizing agent and a pharmaceutically acceptable excipient, wherein the allantoin is present in an amount of about 0.5% to about 15% by weight. In some embodiments, a method of treating atopic dermatitis in a patient in need thereof comprises administering a formulation consisting essentially of allantoin, a solvent, an emollient, an emulsifier, an antioxidant, a preservative, a pH modifier, a solubilizing agent and a pharmaceutically acceptable excipient, wherein the allantoin is present in an amount of about 0.5% to about 15% by weight. In some embodiments, a method of treating atopic dermatitis in a patient in need thereof comprises administering a formulation consisting of allantoin, a solvent, an emollient, an emulsifier, an antioxidant, a preservative, a pH modifier, a solubilizing agent and a pharmaceutically acceptable excipient, wherein the allantoin is present in an amount of about 0.5% to about 15% by weight.

Embodiments of the present disclosure also relate to the use of formulations of allantoin in connection with excipients or stabilizers. Stabilizers include carbohydrates, amino acids, fatty acids, and surfactants and are known to those skilled in the art.

Compositions according to the embodiments described herein can contain other, optional ingredients. For example, compositions according to the present embodiments can contain glycerin, lactic acid, lipid-soluble components such as, but not limited to, caprylic/capric triglycerides; steareth-2; steareth-21; polygrlyceryl-3 beeswax; a branched-carboxylic acid ester of a branched-chain alcohol selected from the group consisting of isononyl isononanoate, isodecyl isononanoate, isooctyl isononanotate, isooctyl isooctanoate, isononyl isooctanoate, isodecyl isooctanoate, isononyl isodecanoate, isooctyl isodecanoate, and isodecyl isodecanoate; an acrylates/$C_{10}$-$C_{30}$ alkyl acrylates cross-polymer; methylgluceth-20; a glyceryl ester of a long chain fatty acid selected from the group consisting of glyceryl monostearate, glyceryl monopalmitate, and glyceryl monoarachidate; hydrogenated vegetable oil; squalane; $C_{12}$-$C_{15}$ alkyl benzoates; di-$C_{12}$-$C_{15}$ alkyl fumarate; cholesterol; lanolin alcohol; octyldodecanol, isostearic acid; a branched-chain neopentanoate selected from the group consisting of octyldodecyl neopentanoate, heptyldodecyl neopentanoate, nonyldodecyl neopentanoate, octylundecyl neopentanoate, heptylundecyl neopentanoate, nonylundecyl neopentanoate, octyltridecyl neopentanoate, heptyltridecyl neopentanoate, and nonyltridecyl neopentanoate; an arachidyl ester of a short-chain carboxylic acid selected from the group consisting of arachidyl propionate, arachidyl acetate, arachidyl butyrate, and arachidyl isobutyrate; a long-chain fatty acid ester of a medium-chain alcohol selected from the group consisting of octyl palmitate, octyl myristate, octyl stearate, heptyl palmitate, heptylmyristate, heptyl stearate, nonyl palmitate, nonyl myristate, and nonyl stearate; jojoba oil; a myristyl ester of a long-chain fatty acid selected from the group consisting of myristyl myristate, myristyl laurate, and myristyl palmitate; bisabolol; hydrogenated jojoba oil; jojoba esters; methyl-gluceth-20 sesquistearate; PPG-14 butyl ether; PPG-15 stearyl ether; PPG-1-isoceteth-3-accetate; laureth-2-benzoate; diisostearyl dimmer dilinoleate; a long-chain cis-monounsaturated fatty acid ester of a medium-chain alcohol; a medium-chain saturated carboxylic acid ester of a long-chain alcohol; hydrogenated soy glycerides; a long-chain fatty acid ester of cetyl alcohol selected from the group consisting of cetyl palmitate, cetyl stearate, and cetyl myristate; palm kernel oil; palm oil; and an arachidyl ester such as arachidyl acetate, arachidyl propionate, arachidyl butyrate, or arachidyl isobutyrate.

In addition, the composition can further comprise other ingredients that are generally used in the cosmetic art and in the art of over-the-counter skin preparations. These ingredients include, but are not limited to: (1) other plant extracts, such as horsetail extract, horse chestnut extract, rose extract, or lavender extract; (2) a short-chain carboxylic acid ester of tocopherol selected from the group consisting of tocopheryl acetate, tocopheryl propionate, tocopheryl butyrate, and tocopheryl isobutyrate; (3) a long-chain fatty acid ester of ascorbic acid selected from the group consisting of ascorbyl myristate, ascorbyl palmitate, and ascorbyl stearate; (4) a long-chain fatty acid ester of retinol or a retinol derivative or analogue wherein the acyl moiety of the ester is selected from the group consisting of myristic acid, palmitic acid, and stearic acid; and (5) a sunscreen, which can be at least one compound selected from the group consisting of octyl methoxycinnamate, p-aminobenzoate, glyceryl p-aminobenzoate, p-dimethylaminobenzoic acid, methyl anthranilate, menthyl anthranilate, phenyl anthranilate, benzyl anthranilate, phenylethyl anthranilate, linalyl anthranilate, terpinyl anthranilate, cyclohexenyl anthranilate, amyl salicylate, phenyl salicylate, benzyl salicylate, menthyl salicylate, glyceryl salicylate, dipropyleneglycol salicylate, methyl cinnamate, benzyl cinnamate, α-phenyl cinnamonitrile, butyl cinnamoylpyruvate, umbelliferone, methylacetoumbelliferone, esculetin, methylesculetin, daphnetin, esculin, daphnin, diphenylbutadiene, stilbene, dibenzalacetone, benzalacetophenone, sodium 2-naphthol-3,6-disulfonate, sodium 2-naphthol-6,8-disulfonate, dihydroxynaphthoic acid, salts of dihydroxynaphthoic acid, o-hydroxybiphenyldisulfonates, p-hydroxybiphenyldisulfonates, 7-hydroxycoumarin, 7-methylcoumarin, 3-phenyl-coumarin, 2-acetyl-3-bromoindazole, phenylbenzoxazole, methylnaphthoxazole, arylbenzothiazoles, quinine bisulfate, quinine sulfate, quinine chloride, quinine oleate, quinine tannate, 8-hydroxyquinoline salts, 2-phenylquinoline, hydroxyl-substituted benzophenones, methoxy-substituted benzophenones, uric acid, vilouric acid, tannic acid, tannic acid hexaethylether, hydroquinone, oxybenzone, sulisobenzone, dioxybenzone, benzoresorcinol, 2,2',4,4'-tetrahydroxybenzophenone, 2,2'-dihydroxy-4,4-dimethoxybenzophenone, octabenzone, butylmethoxydibenzoylmethane, etocrylene, and 4-isopropyldibenzoylmethane. Other ingredients can also optionally be included, such as colorants, pigments, opacifiers, and the like.

Methods according to the embodiments described herein provide rapid improvement, are well tolerated by patients, are easy to apply, and can be used alone or with other methods for treatment of skin conditions. Alternative formulations with reduced sodium lauryl sulfate, reduced beeswax and no fragrance are better suited to treat diseases such as Epidermolysis bullosa, where the skin is fragile and sensitive to irritants. It was unexpectedly found that these formulations, though they have reduced sodium lauryl sulfate and reduced beeswax, have a stable emulsion in room temperatures and are effective in treating inflammatory skin conditions. In particular, formulations of embodiments herein have better penetration of intact skin and are able to deliver the active (i.e. allantoin) across intact skin.

In any of the foregoing embodiments, the composition can further include fragrance. The use of fragrance is well known in the art of over-the-counter drug formulation, and many suitable fragrances are known in the art. The stability and function of the composition is not altered by the presence or absence of fragrance. In many alternatives, it may be desirable to avoid the use of fragrance which may trigger allergic reaction in patients predisposed to such reactions. Accordingly, in certain embodiments, the composition excludes a fragrance.

The compositions can further include other ingredients, such as proteins, humectants, other preservatives, essential oils, other vitamins, colorants, hydroxyacids, other plant extracts, sunscreens, sodium hyaluronate, lipids, fatty acids, thickeners, panthenol, and the like. The use of such components is conventional in the over-the-counter drug art. Typical sunscreens are octyl methoxycinnamate and benzophenone-3.

In any of the foregoing embodiments, the term "inflammatory skin conditions" is used interchangeably with "inflammatory skin diseases" and includes cutaneous porphyria, sclerodema, epidermolysis bullosa, psoriasis, decubitus ulcers, pressure ulcers, diabetic ulcers, venous stasis ulcers, sickle cell ulcers, ulcers caused by burns, eczema, urticaria, atopic dermatitis, dermatitis herpetiform, contact dermatitis, arthritis, gout, lupus erythematosus, acne, alopecia, carcinomas, psoriasis, rosacea, miliaria, skin infections, post-operative care of incisions, post-operative skin care following any variety of plastic surgery operations, skin care following radiation treatment, care of dry, cracked or aged skin and skin lines as well as other conditions affecting the skin and having an inflammatory component. The term may also include symptoms associated with such diseases such as, without limitation, pain, scarring, inflammation, redness, milia, itching, skin thickening, blisters, or other symptoms associated with inflammatory disease.

Pharmaceutical Compositions.

Pharmaceutical compositions provided by the present disclosure may comprise formulations of allantoin and in certain embodiments, in purified form, together with a suitable amount of one or more pharmaceutically acceptable vehicles, so as to provide a composition for proper administration to a patient with an inflammatory skin disease. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions may also contain wetting agents, emulsifying agents, and/or pH buffering agents. In addition, auxiliary, stabilizing, thickening, lubricating, and/or coloring agents may be used. Other examples of suitable pharmaceutical vehicles are described in the art (see, for example, "Remington's Pharmaceutical Sciences," Lippincott Williams & Wilkins, 21st Edition, 2005).

Pharmaceutical compositions disclosed herein may be prepared by standard mixing techniques, such as are conventional in the cosmetic art and in the art of over-the-counter drug formulation for blending lipid-soluble components and water-soluble components. These mixing techniques include both manual and mechanical mixing, and include homogenization mixing and sweep mixing. The mixing techniques to be used can be chosen by one of ordinary skill in the art based on variables such as the viscosity of the components to be mixed and the volume of those components, as well as the relative proportion of lipid-soluble and water-soluble ingredients. The composition can be mixed in two or more batches, such as one batch containing lipid-soluble ingredients and another batch containing water-soluble ingredients, and the batches can then be mixed at the final state of preparation.

For example, pharmaceutical compositions disclosed herein may be manufactured by following these steps: (1) mix and heat water, 30% solution of sodium lauryl sulfate, propylene glycol, tetrasodium EDTA and citric acid in one container ("Container 1"); (2) in another container ("Container 2"), mix and heat lanolin oil, beeswax, stearyl alcohol and cetyl alcohol; (3) when both containers reach about 170-180° F., add contents of Container 2 to Container 1; (4) add cod liver oil and butyl hydroxytoluene (BHT); (5) mix for about thirty minutes; (6) add allantoin; (7) mix for about thirty minutes; (8) cool contents to about 120° F.; (9) add methylparaben and propylparaben; (10) mix for about ten minutes; (11) remove the mixer and insert the homogenizer; (12) activate the homogenizer for about five minutes; (13) remove the homogenizer and insert mixer; (14) mix for about thirty minutes while maintaining temperature range of about 115-120° F.; (15) continue mixing while contents are cooled to about 115° F.; (16) stop mixing when contents reach about 115° F.; (17) remove mixer and cover drum; (18) store cream overnight at room temperature; and (19) package the cream into finished product containers.

Pharmaceutical compositions may be formulated in a conventional manner using one or more physiologically acceptable carriers, diluents, excipients, or auxiliaries, which facilitate processing of allantoin and one or more pharmaceutically acceptable vehicles into formulations that can be used pharmaceutically. Proper formulation is dependent upon the route of administration chosen.

Pharmaceutical compositions provided by the present disclosure may be administered for therapeutic or prophylactic treatments. A therapeutic amount is an amount sufficient to remedy a disease state or symptoms, or otherwise prevent, hinder, retard, or reverse the progression of disease or any other undesirable symptoms in any way whatsoever. In prophylactic applications, pharmaceutical compositions or the present disclosure may be administered to a patient susceptible to or otherwise at risk of a particular disease or infection. Hence, a prophylactically effective amount is an amount sufficient to prevent, hinder or retard a disease state or its symptoms.

Specific modes of administration will depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician).

Pharmaceutical formulations containing the above-described compound and a suitable carrier can be topical dosage forms which include, but are not limited to, solutions, powders, fluid emulsions, fluid suspensions, semi-solids, ointments, pastes, creams, gels and jellies, and foams comprising an effective amount of a polymer or copolymer of the present embodiment. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, Modem Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980) can be consulted.

The embodiments illustrating the methods and materials used may be further understood by reference to the following non-limiting examples.

Example 1

A formulation containing 3.0% allantoin; 67.01% water; 3.5% cetyl alcohol; 1.7% stearyl alcohol; 2.5% beeswax; 0.09% citric acid; 10.6% lanolin oil; 5.7% propylene glycol; 0.15% tetrasodium EDTA; 2% cod liver oil; 0.5% butylated hydroxytoluene; 0.3% methylparaben; 0.25% propylparaben; 0.2% fragrance; and 2.5% sodium lauryl sulfate in a 30% solution was made. The pH of this formulation is 4.58.

Example 2

A formulation containing 3.0% allantoin; 67.41% water; 4.2% cetyl alcohol; 2% stearyl alcohol; 1.9% beeswax; 0.09% citric acid; 10.6% lanolin oil; 5.7% propylene glycol; 0.15% tetrasodium EDTA; 2% cod liver oil; 0.5% butylated hydroxytoluene; 0.3% methylparaben; 0.25% propylparaben; and 1.9% sodium lauryl sulfate in a 30% solution was made. The pH of this formulation is 4.54. It is desirous to reduce irritants due to the indications of these inflammatory skin conditions; thus we reduced the amounts of beeswax, and sodium lauryl sulfate and removed the fragrance. It was unexpected that such a reduction of these ingredients created an effective composition because lowering the emulsifier concentration may not result in a system that demonstrates long-term stability.

Example 3

A formulation containing 3.0% allantoin; water; cetyl alcohol; stearyl alcohol; beeswax; 0.09% citric acid; 10.6% lanolin oil; 5.7% propylene glycol; 0.15% tetrasodium EDTA; 2% cod liver oil; 0.5% butylated hydroxytoluene; 0.3% methylparaben; 0.25% propylparaben; and 1.5% sodium lauryl sulfate in a 30% solution was made. It is desirous to reduce irritants due to the indications of these inflammatory skin conditions; thus we reduced the amounts of beeswax, and sodium lauryl sulfate and removed the fragrance. It was unexpected that such a reduction of these ingredients created an effective composition because lowering the emulsifier concentration may not result in a system that demonstrates long-term stability at room temperature.

Example 4

A formulation containing 6.0% allantoin; 63.98% water; 3.23% cetyl alcohol; 1.5% stearyl alcohol; 2.75% beeswax; 0.09% citric acid; 10.6% lanolin oil; 5.7% propylene glycol; 0.15% tetrasodium EDTA; 2% cod liver oil; 0.5% butylated hydroxytoluene; 0.3% methylparaben; 0.25% propylparaben; 0.2% fragrance; and 2.75% sodium lauryl sulfate in a 30% solution was made. The pH of this formulation is 4.62.

Example 5

A formulation containing 6.0% allantoin; 64.81% water; 3.5% cetyl alcohol; 1.5% stearyl alcohol; 2.3% beeswax; 0.09% citric acid; 10.6% lanolin oil; 5.7% propylene glycol; 0.15% tetrasodium EDTA; 2% cod liver oil; 0.5% butylated hydroxytoluene; 0.3% methylparaben; 0.25% propylparaben; and 2.3% sodium lauryl sulfate in a 30% solution was made. The pH of this formulation is 4.51. It is desirous to reduce irritants due to the indications of these inflammatory skin conditions; thus we reduced the amounts of beeswax, and sodium lauryl sulfate and removed the fragrance. It was unexpected that such a reduction of these ingredients created an effective composition because lowering the emulsifier concentration may not result in a system that demonstrates long-term stability at room temperature.

Example 6

A formulation containing 6.0% allantoin; 65.11% water; 3.6% cetyl alcohol; 1.7% stearyl alcohol; 2.0% beeswax; 0.09% citric acid; 10.6% lanolin oil; 5.7% propylene glycol; 0.15% tetrasodium EDTA; 2% cod liver oil; 0.5% butylated hydroxytoluene; 0.3% methylparaben; 0.25% propylparaben; and 2.0% sodium lauryl sulfate in a 30% solution was made. It is desirous to reduce irritants due to the indications of these inflammatory skin conditions; thus we reduced the amounts of beeswax, and sodium lauryl sulfate and removed the fragrance. It was unexpected that such a reduction of these ingredients created an effective composition because lowering the emulsifier concentration may not result in a system that demonstrates long-term stability at room temperature.

Example 7

This formulation contained 9.0% allantoin; 61.78% water; 2.7% cetyl alcohol; 1.2% stearyl alcohol; 2.75% beeswax; 0.12% citric acid; 10.6% lanolin oil; 5.7% propylene glycol; 0.15% tetrasodium EDTA; 2% cod liver oil; 0.5% butylated hydroxytoluene; 0.3% methylparaben; 0.25% propylparaben; 0.2% fragrance; and 2.75% sodium lauryl sulfate in a 30% solution. The pH of this formulation is 4.07.

Example 8

This formulation contained 9.0% allantoin; water; cetyl alcohol; stearyl alcohol; beeswax; citric acid; 10.6% lanolin oil; 5.7% propylene glycol; 0.15% tetrasodium EDTA; 2% cod liver oil; 0.5% butylated hydroxytoluene; 0.3% methylparaben; 0.25% propylparaben; and sodium lauryl sulfate in a 30% solution. It is desirous to reduce irritants due to the indications of these inflammatory skin conditions; thus we reduced the amounts of beeswax, and sodium lauryl sulfate and removed the fragrance. It was unexpected that such a reduction of these ingredients created an effective composition because lowering the emulsifier concentration may not result in a system that demonstrates long-term stability at room temperature.

Example 9

This formulation contained 9% allantoin; 63.71% water; 2.5% cetyl alcohol; 1.2% stearyl alcohol; 2.0% beeswax; 0.09% citric acid; 10.6% lanolin oil; 5.7% propylene glycol; 0.15% tetrasodium EDTA; 2% cod liver oil; 0.5% butylated hydroxytoluene; 0.3% methylparaben; 0.25% propylparaben; and 2.0% sodium lauryl sulfate in a 30% solution. It is desirous to reduce irritants due to the indications of these inflammatory skin conditions; thus we reduced the amounts of beeswax, and sodium lauryl sulfate and removed the fragrance. It was unexpected that such a reduction of these ingredients created an effective composition because lowering the emulsifier concentration may not result in a system that demonstrates long-term stability at room temperature.

Example 10

The formulations A.S. 1-139E, A.S. 1-81B, A.S. 1-135C, A.S. 1-1350, and A.S. 1-81G were tested on a minimum of triplicate sections from three different cadaver skin donors and three different porcine skin donors for the percutaneous absorption of allantoin over a 48-hour dose period. The intent of this study was to mimic the absorption of allantoin directly into the capillary bed, while the dermis only study attempted to mimic the loss of skin barrier function due to broken skin or blisters. In addition, each formulation was tested in at least triplicate membrane chambers. At preselected times after dosing, the dermal receptor solution was removed in its entirety, replaced with fresh receptor solution, and an aliquot saved for subsequent analysis. The samples were analyzed for the allantoin using high performance liquid chromatography with UV and MS detection (HPLC-UV-MS). The summary results are presented in FIG. 3 and FIG. 4. The bottom table of FIG. 3 lists a remanufacture of the 9% allantoin cream (A.S. 1-153H) to achieve a better viscosity of the final product. That table demonstrates that the initial results with A.S. 1-81G were lower than expected and unreliable due to problems in the manufacture of this lot. The remanufacture of the new A.S. 1-153H 9% lot demonstrated no viscosity issues, and was retested in the full thickness skin model only, demonstrating that the penetration of allantoin with this concentration was two times that of the 6% formulation (A.S. 1-135G). It can also be inferred based on this result that the 9% cream results in the top table of FIG. 3 may be higher than reported with A.S. 1-81G and dose related to the other formulation concentrations in all percutaneous models.

Figure 6:
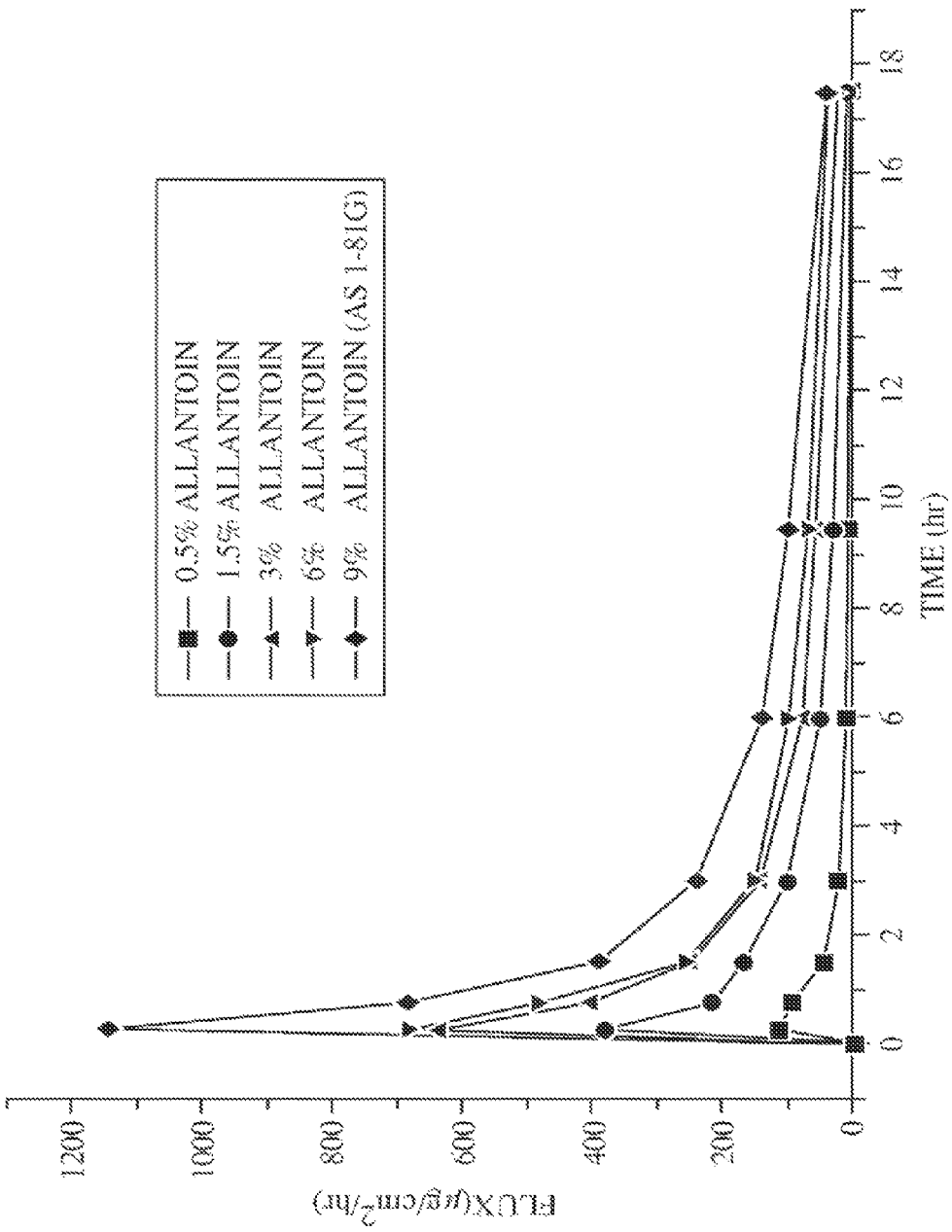
FIG. 6 is a graph of the results of membrane release of different formulations of allantoin through a porous membrane.
Figure 8:
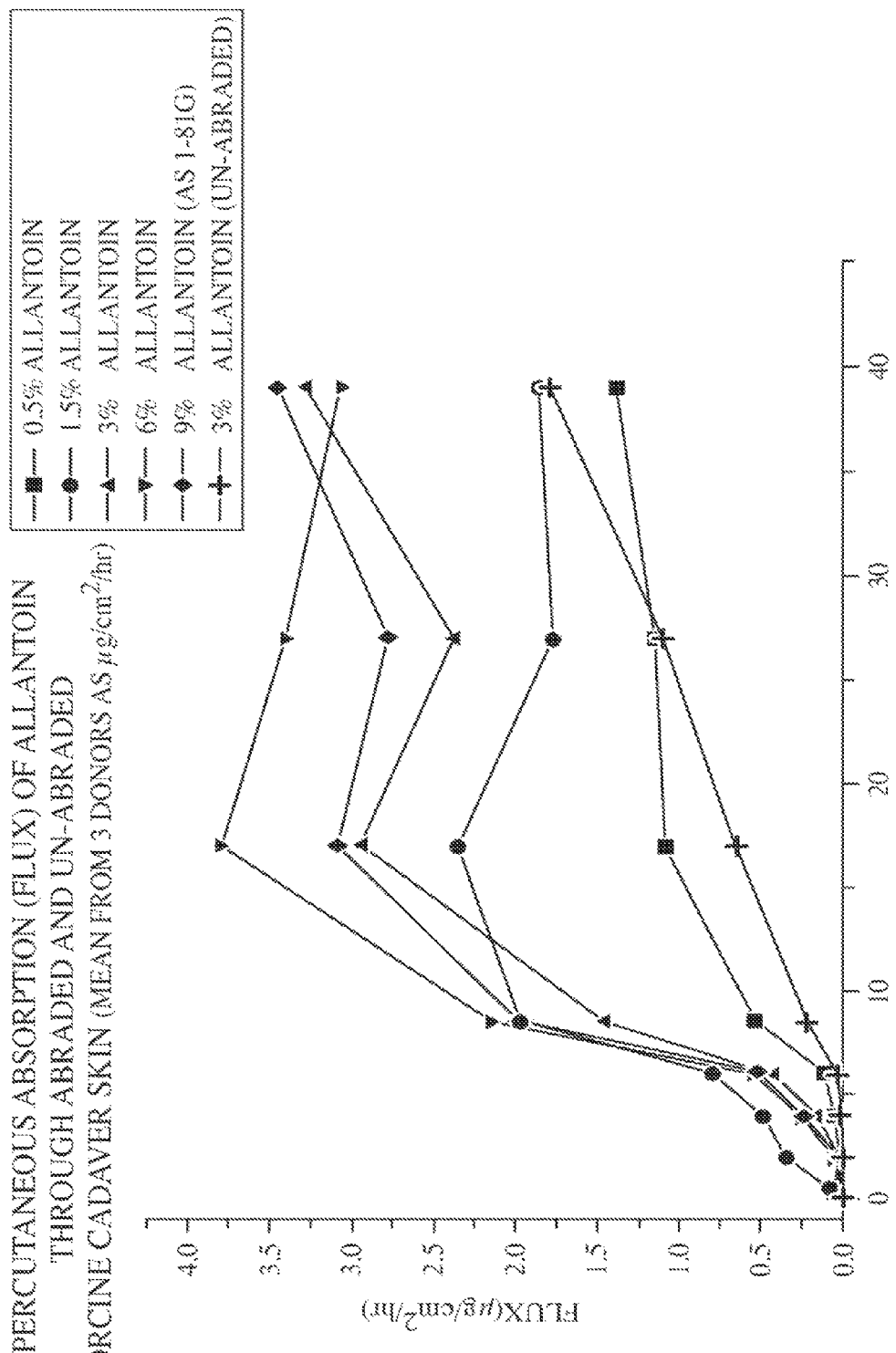
FIG. 8 is a graph of the results for the percutaneous absorption of different formulations of allantoin through abraded and unabraded porcine cadaver skin.
Figure 12:
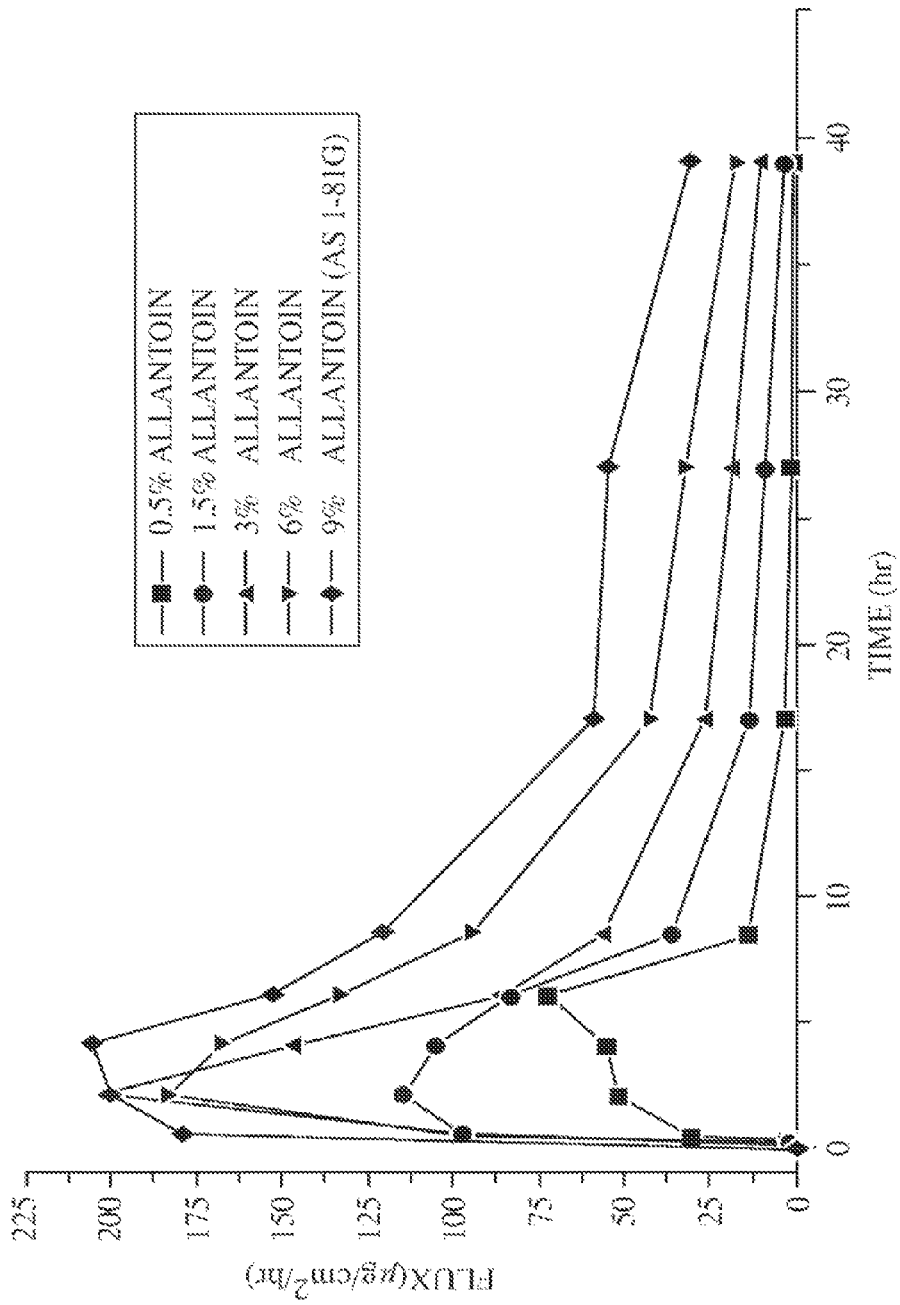
FIG. 12 is a graph summarizing the percutaneous absorption of different formulations of allantoin through the isolated dermis layer from human cadaver skin.
Figure 14:
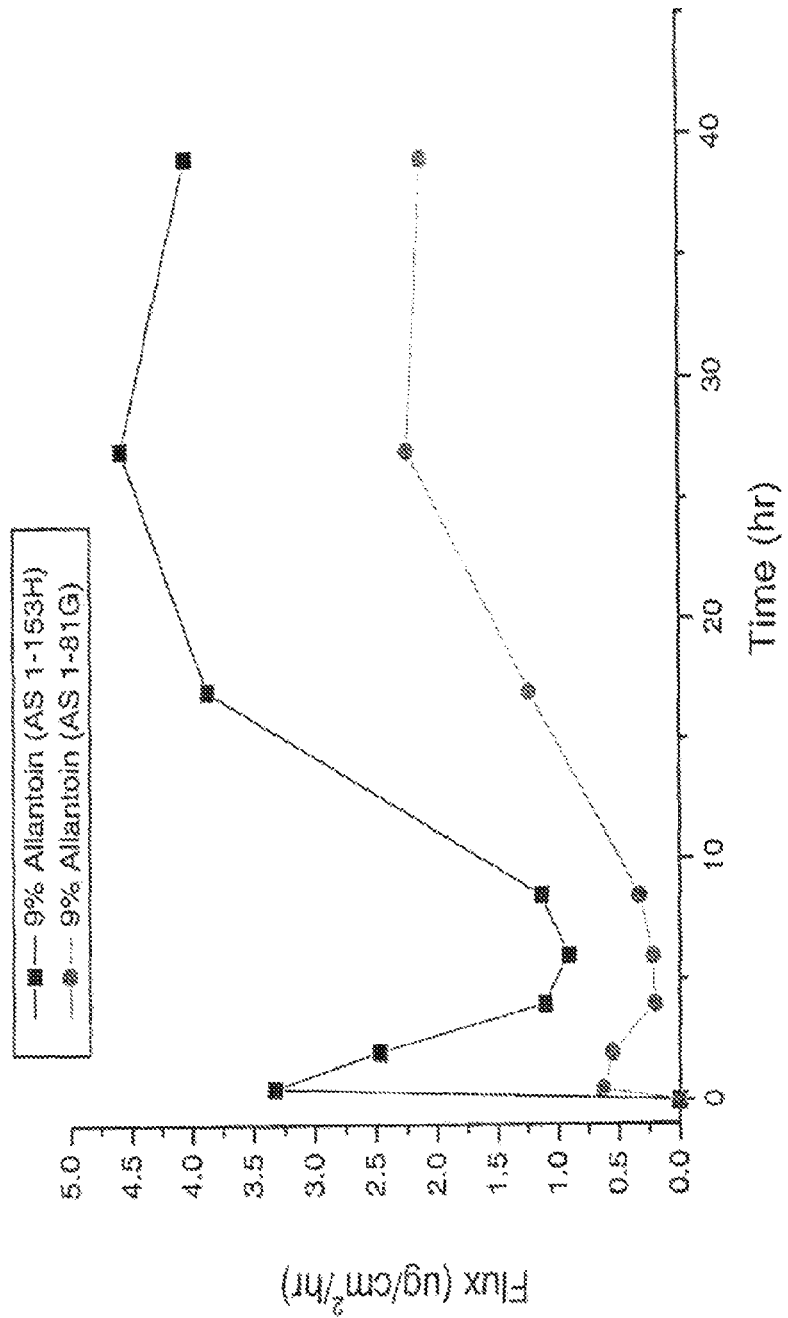
FIG. 14 is a graph summarizing the percutaneous absorption of 9% allantoin through the isolated dermis layer from human cadaver skin.

Conclusions: Analysis of the mass delivered through the porous membrane over 24 hours (FIGS. 6-7) showed that 9%>6%>3%>1.5%>0.5% ($p<0.05$). Area under the curve presented graphically demonstrated a dose-related increase in allantoin penetration across the membrane. Analysis of the mass delivered through full thickness human cadaver skin (FIGS. 10-11) showed that 6% delivered more than 0.5% ($p<0.05$), and that penetration across the skin was related to the concentration of allantoin in the formulation. The accuracy of the formulation's manufacturing impacted the ability of the formulation to deliver allantoin across the skin, as demonstrated by a 2× increase in allantoin delivered across the intact skin with the new 9% lot (A.S.-153H) versus the previous 9% lot (A.S.1-81G), which was outside of specifications in terms of physical appearance and consistency.

Statistical analysis of the mass delivered through dermis only human cadaver skin (FIGS. 12-15) showed that 9%>6%>3%>1.5%>0.5% (p<0.05). It is well known from studies with dermal formulations that the lack of efficacy of dermal products is due to lack of penetration of the active ingredient across the stratum corneum, which is an effective barrier, however the formulations described above delivered allantoin across this stratum corneum in a dose related manner, unexpectedly. When the skin's barrier has been damaged or removed (as seen with the isolated dermis in FIGS. 12-15), the penetration of allantoin increases significantly.

Blood and urine collection and analysis for the presence of allantoin demonstrated no increase in basal levels of allantoin in either the blood or urine from EB patients treated with 1.5% allantoin daily for a period greater than 1 year. In addition, data derived from various skin penetration models (dermis and full thickness cadaver skin, abraded porcine skin, and membrane) demonstrated a dose-related increase in allantoin concentrations across various skin models, which was clearly unexpected due to lack of penetration enhancers in the formulation. Specifically, allantoin levels increased from 1.5 to 3× across the dermis in the 3%, 6%, and 9% formulations; 2.5 to 7× across the full thickness skin; and 2-4× across the membrane, as compared to a 1.5% formulation. Additionally, it was unexpected that the allantoin formulations result in penetration of allantoin across the skin membrane without any increase in systemic blood levels.

The results of the penetration studies with the various concentration of the active ingredient, allantoin, was clearly unexpected, given the robustness of the protection of the skin from penetration of topical products. This formulation was able to deliver allantoin across all skin models in a dose-related manner over a sustained period of time. The inability of deliver of active ingredients across the intact skin and dermal barriers is the reason why topical products typically only work on superficial skin diseases.

Example 11

In vitro tests confirm the protein dispersing activity of allantoin as measured by the concentration of reactive sulphydryl groups released from the protein of skin samples. Keratolytic activity on psoriatic scales was demonstrated in vitro by incubation with concentrations as low as 0.2% allantoin solution. (Fisher A 1981; Cajkovac et al 1992). Keratolysis is a process whereby horny cells are dispersed with a release of non-keratinous material such as free amino acids and acid mucopolysaccharides which contributes to the horny layer associated with psoriasis (Flesch 1958). Other studies have further demonstrated the ability of allantoin to remove or reduce calluses and other forms of hyperkeratization by dissolving the cement holding the cornified cells together, or loosening of the desmosomes as lower concentrations (<1%) (protein bridges) (Mecca SB 1976). All of these in vitro studies have suggested that allantoin could be effective in psoriasis, but no published clinical data to date with allantoin administration topically have demonstrated efficacy in psoriasis. Results from testing of this topical formulation at a concentration of allantoin up to 1.5% in clinical psoriasis was consistent with published data on the lack of human clinical efficacy with topically administered allantoin. However, unexpectedly, evaluation of allantoin at a daily administration of this formulation at a higher concentration (3%), which has been shown to deliver allantoin across the skin barriers, demonstrated complete clearing of psoriatic plaques in addition to prevention of reoccurrence of plaque formation.

The results of the 3% study demonstrate the ability of allantoin to effectively close wounds and lesions, and significantly lower than body surface area coverage of lesions and wounds in patients with this indication. Two patients in this study had previously used the 1.5% formulation for an extended period of time, and noted that, while the 1.5% formulation was effective, application of the 3% cream was more effective in closure of wounds and the healing time was faster. These results are consistent with the findings from the percutaneous skin studies, in that allantoin can be delivered to the active site more effectively at higher cream concentrations resulting in improved efficacy.

Example 12

Eight patients 6 months to 4 years of age were enrolled an open study with a 3 month treatment period involving daily administration of 3% allantoin cream to all areas of the body containing blisters, skin erosions and open wounds: 3 patients with EB Simplex; 3 patients with Junctional EB; 2 patients with Recessive Dystrophic EB. All patients had between 25-75% of body surface area affected by the disease.

Measurements: The key measurements were based on a change in disease condition from baseline/screening evaluations: (1) the change from baseline in size of an index lesion/wound measured by area, cm squared; (2) the change from baseline in affected body surface area (BSA) including head, upper limbs, lower limbs, and trunk; physicians global assessment of improvement from baseline measured on a 6 point scale (Clear; Excellent; Marked; Good; None; Worsening).

Results: The findings of the study indicated that there were clinically significant improvements in BSA and Index lesion scores compared with baseline. Following 3 months of treatment, there was a 55% reduction in BSA ratings from baseline and in most patients one or more index lesions were totally healed/cleared. The Physicians Global Assessment of Improvement indicated that all patients improved from baseline with some patients showing as much as a 75% improvement. In addition, the cream appeared to prevent the recurrence of newly formed blisters and erosions.

CONCLUSIONS

The findings of the study indicated that a 3% concentration of allantoin in a cream formulation induces a clinically significant change in the severity of the disease including wound closures and an overall reduction of body blisters and skin erosions. A number of these patients had been exposed previously to a 1.5% concentration of allantoin cream which was felt to be less efficacious. The current formulation promotes the penetration of allantoin across the skin barrier thereby increasing effectiveness in a dose related manner. Based on the dose-related effects seen with this formulation, it is likely that higher concentrations may confer even better efficacy.

Although the present invention has been described in considerable detail with reference to certain preferred embodiments thereof, other versions are possible. Accordingly, the present embodiments are to be considered as illustrative and not restrictive. Therefore the spirit and scope of the appended claims should not be limited to the description and the preferred versions contained within this specification.

The invention claimed is:

1. A method for treating or reducing reoccurrence of psoriasis in a patient in need thereof comprising contacting the patient's skin with an effective amount of a composition comprising allantoin in an amount from about 3.0% to about 15% by weight; an emollient; an emulsifier; citric acid; propylene glycol; butylated hydroxytoluene (BHT); a preservative which is selected from the group consisting of methylparaben, propylparaben, and a combination thereof; tetrasodium EDTA; a viscosity enhancing agent which is selected from the group consisting of cetyl alcohol, stearyl alcohol, and a combination thereof; and water, wherein the composition is an oil-in-water emulsion and does not contain coal tar.

2. The method of claim 1, wherein the composition is administered to the subject daily.

3. The method of claim 1, wherein the allantoin is in an amount of about 3.0% to about 9.0%.

4. The method of claim 1, wherein the composition results in penetration of the allantoin across the skin membrane of the patient in a dose dependent manner.

5. The method of claim 1, wherein the composition results in penetration of the allantoin across the skin membrane of the patient without an increase in systemic blood levels of allantoin in the patient.

6. The method of claim 1, wherein the emollient is selected from the group consisting of lanolin oil, cod liver oil, mineral oil, an alcohol, and any combination thereof.

7. The method of claim 1, wherein the emulsifier is selected from the group consisting of sodium lauryl sulfate, a white wax, and a combination thereof.

8. The method of claim 1, wherein the pH of the composition is about 4.0 to about 5.5 at room temperature.

9. A method for reducing or clearing psoriatic plaques in a patient in need thereof comprising contacting the plaques with an effective amount of a composition comprising allantoin in an amount from about 3.0% to about 15% by weight; an emollient; an emulsifier; citric acid; propylene glycol; butylated hydroxytoluene (BHT); a preservative which is selected from the group consisting of methylparaben, propylparaben, and a combination thereof; tetrasodium EDTA; a viscosity enhancing agent which is selected from the group consisting of cetyl alcohol, stearyl alcohol, and a combination thereof; and water, wherein the composition is an oil-in-water emulsion and does not contain coal tar.

10. The method of claim 9, wherein the composition is administered to the subject daily.

11. The method of claim 9, wherein the allantoin is in an amount of about 3.0% to about 9.0%.

12. The method of claim 9, wherein the composition results in penetration of the allantoin across the skin membrane of the patient in a dose dependent manner.

13. The method of claim 9, wherein the composition results in penetration of the allantoin across the skin membrane of the patient without an increase in systemic blood levels of allantoin in the patient.

14. The method of claim 9, wherein the emollient is selected from the group consisting of lanolin oil, cod liver oil, mineral oil, an alcohol, and any combination thereof.

15. The method of claim 9, wherein the emulsifier is selected from the group consisting of sodium lauryl sulfate, a white wax, and a combination thereof.

16. The method of claim 9, wherein the pH of the composition is about 4.0 to about 5.5 at room temperature.

* * * * *